(12) United States Patent
Hale

(10) Patent No.: US 6,706,711 B2
(45) Date of Patent: Mar. 16, 2004

(54) PYRAZOLE DERIVED KINASE INHIBITOR

(75) Inventor: Michael R. Hale, Bedford, MA (US)

(73) Assignee: Vertex Pharmaceuticals Incorporated, Cambridge, MA (US)

( * ) Notice: Subject to any disclaimer, the term of this patent is extended or adjusted under 35 U.S.C. 154(b) by 0 days.

(21) Appl. No.: 10/134,361

(22) Filed: Apr. 26, 2002

(65) Prior Publication Data

US 2003/0134888 A1 Jul. 17, 2003

Related U.S. Application Data

(60) Provisional application No. 60/287,039, filed on Apr. 27, 2001.

(51) Int. Cl.[7] ............... A61K 31/5377; B61P 35/00; C07D 401/14; C07D 413/12
(52) U.S. Cl. ............... 514/236.5; 544/140; 544/371; 546/175; 546/193; 546/211; 546/256; 546/271.7; 546/269.7; 546/272.7; 546/275.4; 548/312.4; 548/365.7; 548/371.7
(58) Field of Search ............... 544/140; 546/256, 546/275.4; 548/365.7, 371.7; 514/236.5

(56) References Cited

U.S. PATENT DOCUMENTS 5,057,534 A * 10/1991 Taylor et al. ............ 548/371.7

FOREIGN PATENT DOCUMENTS

| JP | 62-195366 | 8/1987 |
|---|---|---|
| JP | 64-40832 | 2/1989 |
| JP | 03-293663 | 12/1991 |
| JP | 04-20955 | 1/1992 |
| WO | WO 98/52941 | 11/1998 |

OTHER PUBLICATIONS

Vishnu Ji Ram et al., "Amino azoles and azole–azines as potential hepatoprotectants: Part III," *Bioorg. Med. Chem. Lett.*, 5:14, pp. 1537–1540 (1995).

Yoshinori Tominaga et al., "Synthesis of 3–aminopyrazolo [3,4–d]pyrimidine derivatives using N–bis(methylthio)methylene–p–toluenesulfonamide," *J. Heterocycl. Chem.*, 27:5, pp. 1245–1248 (1990).

Yoko Nagaoka et al., "Silver halide color photographic material," Online Chemical Abstracts Service, Database Accession Number 117:140489 (1992).

Shuji Kida et al., "Silver halide color photographic material containing 3–amino–5–iminopyrazole derivatives," Online Chemical Abstracts Service, Database Accession Number 116:224634 (1991).

Shigeki Yokoyama et al., "Pyrazoloazole azomethine dyes for photography and filters," Online Chemical Abstracts Service, Database Accession Number 111:176197 (1989).

Hajime Wada et al., "Preparation of 5–hydrazino–1H–pyrazoles as intermediates for 1H–pyrazolo[3,2–c]–s–triazole couplers," Online Chemical Abstracts Service, Database Accession Number 109:190408 (1987).

* cited by examiner

*Primary Examiner*—Robert W. Ramsuer
(74) *Attorney, Agent, or Firm*—Fish & Neave; James F. Haley, Jr.; Denise Bergin

(57) ABSTRACT

Described herein are compounds that are useful as protein kinase inhibitors having the formula:

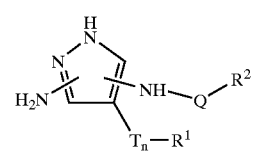

I wherein $R^1$, $R^2$, T, n and Q are as described in the specification. The compounds are useful for treating diseases in mammals that are alleviated by a protein kinase inhibitor, particularly diseases, such as cancer, inflammatory disorders, restenosis, and cardiovascular disease.

28 Claims, No Drawings

PYRAZOLE DERIVED KINASE INHIBITOR

CROSS REFERENCE TO RELATED APPLICATION

This application claims priority to U.S. Provisional Patent Application No. 60/287,039 filed Apr. 27, 2001, the contents of which are incorporated herein by reference.

FIELD OF THE INVENTION

The present invention is in the field of medicinal chemistry and relates to pyrazole compounds that are protein kinase inhibitors, especially inhibitors of ERK, compositions containing such compounds and methods of use. The compounds are useful for treating cancer and other diseases that are alleviated by protein kinase inhibitors.

BACKGROUND OF THE INVENTION

Mammalian mitogen-activated protein (MAP) kinases are serine/threonine kinases that mediate intracellular signal transduction pathways (Cobb and Goldsmith, 1995, *J. Biol. Chem.*, 270, 14843; Davis, 1995, *Mol. Reprod. Dev.* 42, 459). Members of the MAP kinase family share sequence similarity and conserved structural domains, and include the ERK2 (extracellular signal regulated kinase), JNK (Jun N-terminal kinase) and p38 kinases. JNKs and p38 kinases are activated in response to the pro-inflammatory cytokines TNF-alpha and interleukin-1, and by cellular stress such as heat shock, hyperosmolarity, ultraviolet radiation, lipopolysaccharides and inhibitors of protein synthesis (Derijard et al., 1994, *Cell* 76, 1025; Han et al., 1994, *Science* 265, 808; Raingeaud et al., 1995, *J Biol. Chem.* 270, 7420; Shapiro and Dinarello, 1995, *Proc. Natl. Acad. Sci. USA* 92, 12230). In contrast, ERKs are activated by mitogens and growth factors (Bokemeyer et al. 1996, *Kidney Int.* 49, 1187).

ERK2 is a widely distributed protein kinase that achieves maximum activity when both Thr183 and Tyr185 are phosphorylated by the upstream MAP kinase kinase, MEK1 (Anderson et al., 1990, *Nature* 343, 651; Crews et al., 1992, *Science* 258, 478). Upon activation, ERK2 phosphorylates many regulatory proteins, including the protein kinases Rsk90 (Bjorbaek et al., 1995, *J. Biol. Chem.* 270, 18848) and MAPKAP2 (Rouse et al., 1994, *Cell* 78, 1027), and transcription factors such as ATF2 (Raingeaud et al., 1996, *Mol. Cell Biol.* 16, 1247), Elk-1 (Raingeaud et al. 1996), c-Fos (Chen et al., 1993 *Proc. Natl. Acad. Sci. USA* 90, 10952) and c-Myc (Oliver et al., 1995, *Proc. Soc. Exp. Biol. Med.* 210, 162). ERK2 is also a downstream target of the Ras/Raf dependent pathways (Moodie et al., 1993, *Science* 260, 1658) and may help relay the signals from these potentially oncogenic proteins. ERK2 has been shown to play a role in the negative growth control of breast cancer cells (Frey and Mulder, 1997, *Cancer Res.* 57, 628) and hyperexpression of ERK2 in human breast cancer has been reported (Sivaraman et al., 1997, *J Clin. Invest.* 99, 1478). Activated ERK2 has also been implicated in the proliferation of endothelin-stimulated airway smooth muscle cells, suggesting a role for this kinase in asthma (Whelchel et al., 1997, *Am. J. Respir. Cell Mol. Biol.* 16, 589).

Substituted pyrazole derivatives have been described as p38 inhibitors (WO 98/52941). However, there is a high, unmet medical need to develop new therapeutic treatments that are useful in treating the various conditions associated with ERK activation. For many of these conditions the currently available treatment options are inadequate. Accordingly, there is great interest in new and effective inhibitors of protein kinase, including ERK inhibitors that are useful in treating various conditions associated with protein kinase activation.

SUMMARY OF THE INVENTION

The present invention provides compounds and compositions thereof that are useful as protein kinase inhibitors, especially as inhibitors of ERK. These compounds can be used alone or in combination with other therapeutic or prophylactic agents, such as antibiotics, immunomodulators or other anti-inflammatory agents, for the treatment or prophylaxis of diseases mediated by protein kinases, including ERK2. According to a preferred embodiment, the compounds of this invention are capable of binding to the active site of ERK2 and inhibiting the activity of that enzyme.

It is a principal object of this invention to provide compounds that are protein kinase inhibitors represented by formula I:

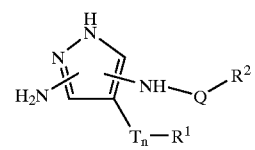

I or a pharmaceutically acceptable salt or derivative thereof, wherein:

T is selected from —NH—, —NHC(O)—, —NHC(O)O—, —NHC(O)NR—, —NHC(O)NH—, —NHSO$_2$—, —NHSO$_2$NR—, —NHSO$_2$NH—, —NHNR—, —NHNH—, —NHNRC(O)—, —NHNHC(O)—, —NHNRSO$_2$—, or —NHNHSO$_2$—;

n is 0 or 1;

each R is independently selected from an optionally substituted group selected from C$_{1-6}$ aliphatic, C$_{6-10}$ aryl, heteroaryl having 5–10 ring atoms, and heterocyclyl having 3–10 ring atoms;

R$^1$ is selected from hydrogen, —CN, halogen, —N(R$^6$)$_2$, —OR, —OH, or —R;

R$^2$ is selected from —(CH$_2$)$_y$R$^4$—(CH$_2$)$_y$CH(R$^4$)$_2$, —(CH$_2$)$_y$CH(R$^7$)CH(R$^4$)$_2$, —N(R$^3$)$_2$, or —NR$^3$(CH$_2$)$_y$N(R$^3$)$_2$;

Q is selected from —C(O)—, —CO$_2$—, —C(O)C(O)—, —C(O)CH$_2$C(O)—, —C(O)NR—, —SO$_2$—, —SO$_2$NR$^6$—, —NR$^6$—, —NRC(O)—, —NRSO$_2$—, —NRC(O)O—, —NRC(O)NR$^6$—, or —C(O)NR$^6$—;

y is 0–6;

each R$^3$ is independently selected from —R, —R$^6$, —COR$^6$, —CO$_2$R, —CON(R$^6$)$_2$, —SO$_2$R$^6$, —(CH$_2$)$_y$R$^4$, or —(CH$_2$)$_y$CH(R$^4$)$_2$;

each R$^4$ is independently selected from —R, —OR, —CO$_2$R, —(CH$_2$)$_y$N(R$^6$)$_2$, —N(R$^6$)$_2$, —OR$^6$, —SR$^6$, —NR$^6$COR$^6$, —NR$^6$CON (R$^6$)$_2$, —C(O) N(R$^6$)$_2$, —SO$_2$R$^6$, —NR$^6$SO$_2$R$^6$, C(O)R$^6$, —CN, or —SO$_2$N (R$^6$)$_2$;

each R$^6$ is independently selected from hydrogen or an optionally substituted C$_{1-6}$ aliphatic group, or two R$^6$ on the same nitrogen are taken together with the nitrogen to form a 5–8 membered heterocyclyl or heteroaryl ring;

each R$^7$ is selected from —R$^6$, —(CH$_2$)$_w$OR$^6$, —(CH$_2$)$_w$N(R$^3$)$_2$, or —(CH$_2$)$_w$SR$^6$; and each w is independently selected from 0–4.

It is a further objective of this invention to provide pharmaceutical compositions comprising the protein kinase inhibitors of this invention. In a preferred embodiment, the protein kinase inhibitors inhibit ERK2. These compositions may be utilized in methods for treating or preventing a variety of protein kinase-mediated disorders, such as cancer, stroke, diabetes, hepatomegaly, cardiovascular disease including cardiomegaly, Alzheimer's disease, cystic fibrosis, viral disease, autoimmune diseases, atherosclerosis, restenosis, psoriasis, allergic disorders including asthma, inflammation, neurological disorders and hormone-related diseases. Each of the above-described methods is also part of the present invention.

It is a further objective of this invention to provide methods for making the compounds and compositions of this invention.

DESCRIPTION OF THE INVENTION

The present invention relates to compounds of formula I. Accordingly, it has now been found that compounds of this invention and compositions thereof are effective as protein kinase inhibitors, especially as inhibitors of ERK2.

As used herein, the following definitions shall apply unless otherwise indicated. The phrase "optionally substituted" is used interchangeably with the phrase "substituted or unsubstituted." Unless otherwise indicated, an optionally substituted group may have a substituent at each substitutable position of the group, and each substitution is independent of the other. Also, combinations of substituents or variables are permissible only if such combinations result in a chemically stable arrangement.

The term "chemically stable arrangement" or "chemically feasible and stable" as used herein, refers to a compound structure that renders the compound sufficiently stable to allow manufacture and administration to a mammal by methods known in the art. Typically, such compounds are stable at a temperature of 40° C. or less, in the absence of moisture or other chemically reactive conditions, for at least a week.

The term "aliphatic" or "aliphatic group" as used herein means a straight-chain or branched $C_1$–$C_{12}$ hydrocarbon chain that is completely saturated or that contains one or more units of unsaturation, or a monocyclic $C_3$–$C_8$ hydrocarbon or bicyclic $C_8$–$C_{12}$ hydrocarbon that is completely saturated or that contains one or more units of unsaturation, but which is not aromatic (also referred to herein as "carbocycle" or "cycloalkyl"), that has a single point of attachment to the rest of the molecule wherein any individual ring in said bicyclic ring system has 3–7 members. For example, suitable aliphatic groups include, but are not limited to, linear or branched alkyl, alkenyl, alkynyl groups and hybrids thereof such as (cycloalkyl)alkyl, (cycloalkenyl)alkyl or (cycloalkyl)alkenyl.

The terms "alkyl", "alkoxy", "hydroxyalkyl", "alkoxyalkyl", and "alkoxycarbonyl", used alone or as part of a larger moiety includes both straight and branched chains containing one to twelve carbon atoms. The terms "alkenyl" and "alkynyl" used alone or as part of a larger moiety shall include both straight and branched chains containing two to twelve carbon atoms.

The terms "haloalkyl", "haloalkenyl" and "haloalkoxy" means alkyl, alkenyl or alkoxy, as the case may be, substituted with one or more halogen atoms. The term "halogen" means F, Cl, Br, or I.

The term "heteroatom" means nitrogen, oxygen, or sulfur and includes any oxidized form of nitrogen and sulfur, and the quaternized form of any basic nitrogen. Also the term "nitrogen" includes a substitutable nitrogen of a heterocyclic ring. As an example, in a saturated or partially unsaturated ring having 0–3 heteroatoms selected from oxygen, sulfur or nitrogen, the nitrogen may be N (as in 3,4-dihydro-2H-pyrrolyl), NH (as in pyrrolidinyl) or NR$^+$ (as in N-substituted pyrrolidinyl).

The term "aryl" used alone or as part of a larger moiety as in "aralkyl", "aralkoxy," or "aryloxyalkyl," refers to monocyclic, bicyclic and tricyclic carbocyclic ring systems having a total of five to fourteen ring members, wherein at least one ring in the system is aromatic and wherein each ring in the system contains 3 to 7 ring members. The term "aryl" may be used interchangeably with the term "aryl ring".

The term "heterocycle", "heterocyclyl", or "heterocyclic" as used herein means non-aromatic, monocyclic, bicyclic or tricyclic ring systems having five to fourteen ring members in which one or more ring members is a heteroatom, wherein each ring in the system contains 3 to 8 ring members.

The term "heteroaryl", used alone or as part of a larger moiety as in "heteroaralkyl" or "heteroarylalkoxy", refers to monocyclic, bicyclic and tricyclic ring systems having a total of five to fourteen ring members, and wherein: 1) at least one ring in the system is aromatic; 2) at least one ring in the system contains one or more heteroatoms; and 3) each ring in the system contains 3 to 7 ring members. The term "heteroaryl" may be used interchangeably with the term "heteroaryl ring" or the term "heteroaromatic".

An aryl (including aralkyl, aralkoxy, aryloxyalkyl and the like) or heteroaryl (including heteroaralkyl, heteroarylalkoxy and the like) group may contain one or more substituents. Suitable substituents on the unsaturated carbon atom of an aryl, heteroaryl, aralkyl, or heteroaralkyl group are selected from halogen; haloalkyl; —CF$_3$; —R$^8$; —OR$^8$; —SR$^8$, 1,2-methylenedioxy; 1,2-ethylenedioxy; protected OH (such as acyloxy); phenyl (Ph); Ph substituted with R$^8$; —O(Ph); —O(Ph) substituted with R$^8$; —CH$_2$(Ph); —CH$_2$(Ph) substituted with R$^8$; —CH$_2$CH$_2$(Ph); —CH$_2$CH$_2$(Ph) substituted with R$^8$; —NO$_2$; —CN; —N(R$^8$)$_2$; —NR$^8$C(O)R$^8$; —NR$^8$C(O)N(R$^8$)$_2$; —NR$^8$CO$_2$R$^8$; —NR$^8$NR$^8$C(O)R$^8$; —NR$^8$NR$^8$C(O)N(R$^8$)$_2$; —NR$^8$NR$^8$CO$_2$R$^8$; —C(O)C(O)R$^8$; —C(O)CH$_2$C(O)R$^8$; —CO$_2$R$^8$, —C(O)R$^8$; —C(O)N(R$^8$)$_2$; —OC(O)N(R$^8$)$_2$; —S(O)$_2$R$^8$; —SO$_2$N(R$^8$)$_2$; —S(O)R$^8$; —NR$^8$SO$_2$N(R$^8$)$_2$,—NR$^8$SO$_2$R$^8$; —C(=S)N(R$^8$)$_2$; —C(=NH)—N(R$^8$)$_2$; —(CH$_2$)$_y$NHC(O)R$^8$; —(CH$_2$)$_y$R$^8$; —(CH$_2$)$_y$NHC(O)NHR$^8$; —(CH$_2$)$_y$NHC(O)OR$^8$; —(CH$_2$)$_y$NHS(O)R$^8$; —(CH$_2$)$_y$NHSO$_2$R$^8$; —(CH$_2$)$_y$NHC(O)CH (V$_z$—R$^8$) (R$^8$); wherein each R$^8$ is independently selected from H, optionally substituted C$_{1-6}$ aliphatic, an unsubstituted 5–10 membered heteroaryl or heterocyclic ring, phenyl (Ph), —O(Ph), or —CH$_2$(Ph); wherein y is 0–6; z is 0–1; and V is a linker group. When R$^8$ is C$_{1-6}$ aliphatic, it may be substituted with one or more substituents selected from —NH$_2$, —NH(C$_{1-4}$ aliphatic), —N(C$_{1-4}$ aliphatic)$_2$, —S(O) (C$_{1-4}$ aliphatic), —SO$_2$(C$_{1-4}$ aliphatic), halogen, —C$_{1-4}$ aliphatic, —OH, —O—(C$_{1-4}$ aliphatic), nitro, cyano, —CO$_2$H, —CO$_2$(C$_{1-4}$ aliphatic), —O(halo C$_{1-4}$ aliphatic), or -halo(C$_{1-4}$ aliphatic); wherein each C$_{1-4}$ aliphatic is unsubstituted.

An aliphatic group or a non-aromatic heterocyclic ring may contain one or more substituents. Suitable substituents on the saturated carbon of an aliphatic group or of a non-aromatic heterocyclic ring are selected from those listed above for the unsaturated carbon of an aryl or heteroaryl group and the following: =O, =S, =NNHR$^9$, =NN(R$^9$)$_2$, =N—, OR$^9$, =NNHC(O)R$^9$, =NNHCO$_2$(alkyl), =NNHSO$_2$(alkyl), or =NR$^9$, where each R$^9$ is independently selected from hydrogen, or an optionally substituted C$_{1-6}$ aliphatic group. When R$^9$ is C$_{1-6}$ aliphatic, it may be substituted with one or more substituents selected from amino, halogen, nitro, cyano, carboxy, t-butoxy, methoxy, ethoxy, hydroxy, or $CF_3$.

Substituents on the nitrogen of a non-aromatic heterocyclic ring are selected from $-R^{10}$, $-N(R^{10})_2$, $-C(O)R^{10}$, $-CO_2R^{10}$, $-C(O)C(O)R^{10}$, $-C(O)CH_2C(O)R^{10}$, $-SO_2R^{10}$, $-SO_2N(R^{10})_2$, $-C(=S)N(R^{10})_2$, $-C(=NH)-N(R^{10})_2$, and $-NR^{10}SO_2R^{10}$; wherein each $R^{10}$ is independently selected from H, an optionally substituted $C_{1-6}$ aliphatic, optionally substituted phenyl (Ph), optionally substituted $-O(Ph)$, optionally substituted $-CH_2$ (Ph), optionally substituted $-CH_2CH_2(Ph)$, or an unsubstituted 5–6 membered heteroaryl or heterocyclic ring. When $R^{10}$ is a $C_{1-6}$ aliphatic group or a phenyl ring, it may be substituted with one or more substituents selected from $-NH_2$, $-NH(C_{1-4}$ aliphatic) $-N(C_{1-4}$ aliphatic$)_2$, halogen, $-(C_{1-4}$ aliphatic), $-OH$, $-O-(C_{1-4}$ aliphatic), nitro, cyano, $-CO_2H$, $-CO_2(C_{1-4}$ aliphatic), $-O(halo\ C_{1-4}$ aliphatic), or $-halo(C_{1-4}$ aliphatic), wherein each $C_{1-4}$ aliphatic is unsubstituted.

The term "linker group" or "linker" means an organic moiety that connects two parts of a compound. Linkers are comprised of $-O-$, $-S-$, $-NR^*-$, $-C(R^*)_2-$, $-C(O)-$, or an alkylidene chain. The alkylidene chain is a saturated or unsaturated, straight or branched, $C_{1-6}$ carbon chain which is optionally substituted, and wherein up to two non-adjacent saturated carbons of the chain are optionally replaced by $-C(O)-$, $-C(O)C(O)-$, $-C(O)NR^*-$, $-C(O)NR^*NR^*-$, $-CO_2-$, $-OC(O)-$, $-NR^*CO_2-$, $-O-$, $-NR^*C(O)NR^*-$, $-OC(O)NR^*-$, $-NR^*NR^*-$, $-NR^*C(O)-$, $-S-$, $-SO-$, $-SO_2-$, $-NR^*-$, $-SO_2NR^*-$, or $-NR^*SO_2-$; wherein $R^*$ is selected from hydrogen or aliphatic. Optional substituents on the alkylidene chain are as described above for an aliphatic group.

Q connects the secondary amine at the pyrazole ring with $R^2$. Q may form additional interactions within the ERK binding site to further enhance the inhibitory activity of the compound. When Q is a carbonyl-containing moiety, such as $-C(O)-$, $-CO_2-$, $-OC(O)-$, $-C(O)C(O)-$, $-C(O)NH-$, $-CO_2NH-$, $-C(O)NHNH-$, $-NHC(O)-$, $-OC(O)NH-$, or $-NHCO_2-$, or a sulfonyl-containing moiety such as $-SO_2-$, $-SO_2NH-$, or $-NHSO_2-$, the carbonyl or sulfonyl oxygen forms a hydrogen-bond with lysine 54 in the ERK binding site. When Q is a NH-containing moiety, such as $-CH_2NH-$ or $-NHNH-$, the NH-group forms a hydrogen-bond with aspartic acid residue 167 in the ERK binding site. When Q is a hydrophobic group, such as an alkyl chain, $-O-$, or $-S-$, Q forms additional hydrophobic interactions within the ERK binding site.

$R^2$ forms hydrophobic interactions within the binding site of ERK, especially with the side-chain carbons of lysine 54 and aspartic acid 167. $R^2$ may also form hydrophobic interactions with the glycine-rich loop, which is made up of amino acid residues 33–38. When $R^2$ is substituted, the substituents may form further interactions within the binding site to enhance the inhibitory activity of the compound. For example, when a substituent on $R^2$ is a hydrogen-bond donor or a hydrogen-bond acceptor, said substituent forms a hydrogen bond with enzyme-bound water molecules that exist in the binding site.

As used herein, T, when present, connects the pyrazole ring with $R^1$. T may form additional interactions within the ERK binding site to further enhance the inhibitory activity of the compound. When T is a carbonyl-containing moiety such as $-C(O)-$, $-CO_2-$, $-OC(O)-$, $-C(O)C(O)-$, $-C(O)NH-$, $-CO_2NH-$, $-C(O)$ $NHNH-$, $-NHC(O)-$, or $-NHCO_2-$, or a sulfonyl-containing moiety such as $-SO_2-$, $-SO_2NH-$, or $-NHSO_2-$, the carbonyl or sulfonyl oxygen forms a hydrogen-bond with the NH of glutamine 105 in the ERK binding site. When T is NH-containing, such as $-CH_2NH-$ or $-NHNH-$, the NH-group forms a hydrogen-bond with the carbonyl of glutamine 105. When T is a hydrophobic group such as an alkyl chain, $-O-$, or $-S-$, T forms additional hydrophobic interactions with the side-chain carbons of glutamine 105 as well as isoleucine 84.

The binding interactions described herein between the compounds of this invention and the ERK binding site have been determined by molecular modeling programs that are known to those of ordinary skill in the art. These molecular modeling programs include QUANTA [Molecular Simulations, Inc., Burlington, Mass., 1992] and SYBYL [Molecular Modeling Software, Tripos Associates, Inc., St. Louis, Mo., 1992]. As used herein, the amino acid numbering for the ERK enzyme corresponds to the Swiss-Prot database entry for accession #P28482. The Swiss-Prot database is an international protein sequence database distributed by the European Bioinformatics Institute (EBI) in Geneva, Switzerland. The database can be found at www.ebi.ac.uk/swissprot.

It will be apparent to one skilled in the art that certain compounds of this invention may exist in tautomeric forms, all such tautomeric forms of the compounds being within the scope of the invention.

Unless otherwise stated, structures depicted herein are also meant to include all stereochemical forms of the structure; i.e., the R and S configurations for each asymmetric center. Therefore, single stereochemical isomers as well as enantiomeric and diastereomeric mixtures of the present compounds are within the scope of the invention. Unless otherwise stated, structures depicted herein are also meant to include compounds, which differ only in the presence of one or more isotopically enriched atoms. For example, compounds having the present structures except for the replacement of a hydrogen by a deuterium or tritium, or the replacement of a carbon by a $^{13}C$- or $^{14}Q$-enriched carbon are within the scope of this invention.

One embodiment of this invention relates to compounds of formula II:

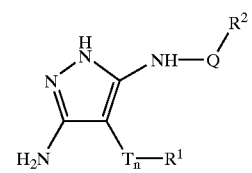

II wherein $R^1$, $R^2$, T, n and Q are as described above.

Preferred T groups, if present, are $-NH-$, $-NHNH-$, $-NHC(O)-$, $-NHCO_2-$, $-NHC(O)NH-$, $-NHSO_2NH-$, or $-NHSO_2-$. In a preferred embodiment, n is zero, and preferred $R^1$ groups of formula II are selected from hydrogen, $N(R^6)_2$, OH, a 3–6 membered carbocyclyl, or an optionally substituted group selected from $C_{1-6}$ aliphatic or a 5–6 membered aryl or heteroaryl ring. When $R^1$ is an optionally substituted phenyl or aliphatic group, preferred substituents on the phenyl or aliphatic group are $R^8$, halo, nitro, alkoxy, and amino. Preferred $T_nR^1$ groups are methyl, ethyl, propyl, cyclopropyl, cyclohexyl, $CH_2OCH_3$, $CH_2OH$, $NH_2$, $NHCH_3$, $NHAc$, $NHAC(O)$ $NHCH_3$, and $CH_2NHCH_3$. More preferred $T_nR^1$ groups of formula II are those listed in the Tables below.

When $R^2$ is $R^4$, preferred $R^4$ groups are pyrrolidin-1-yl, morpholin-4-yl, piperidin-1-yl, and piperazin-1-yl, 4-methyl [1,4]diazepan-1-yl, 4-phenylpiperazine-1-yl, wherein each group is optionally substituted as described above for heterocyclic rings. When $R^2$ is $(CH_2)_yR^4$ or $(CH_2)_yCH(R^4)_2$, preferred $R^4$ groups are further selected from pyridin-3-yl, pyridin-4-yl, imidazolyl, furan-2-yl, 1,2,3,4-tetrahydroisoquinoline, tetrahydrofuran-2-yl, cyclohexyl, phenyl, benzyl, —$CH_2OH$, —$(CH_2)_2OH$, isopropyl, —$CH_2NH_2$, and —$(CH_2)_2NH_2$ wherein each group is optionally substituted. Preferred substituents on $R^4$ are —OH, pyridyl, piperidinyl, and phenyl, wherein phenyl is optionally substituted as described above for aryl rings. When $R^2$ is —$(CH_2)_yCH(R^7)CH(R^4)_2$, preferred $R^7$ groups are $R^6$ and $OR^6$ such as OH and $CH_2OH$ and preferred $R^4$ are as described above. Preferred —$(CH_2)_yCH(R^7)CH(R^4)_2$ groups of formula II are —CH(OH)CH(OH)phenyl and —CH(Me)CH(OH)phenyl. Other preferred —$QR^2$ groups are those listed in the Tables below.

Preferred compounds of formula II are those having one or more, more preferably more than one, and most preferably all, of the features selected from the group consisting of:

(a) $T_nR^1$ is hydrogen, amino, OH, 3–6 membered carbocyclyl, or an optionally substituted group selected from $C_{1-6}$ aliphatic or a 5–6 membered aryl or heteroaryl ring;

(b) Q is —CO—, —$CO_2$—, —CONH—, —$SO_2$—, —$SO_2NH$—, —OC(O)NH—, —C(O)ONH—, or —CONHNH—;

(c) $R^2$ is —$NR^3(CH_2)_yN(R^3)_2$, —$(CH_2)_yR^4$, —$(CH_2)_yCH(R^4)_2$, or —$(CH_2)_yCH(R^7)CH(R^4)_2$;

(d) $R^3$ is R, $R^6$, or —$(CH_2)_yCH(R^4)_2$; and (e) $R^4$ is an optionally substituted group selected from $C_{1-6}$ aliphatic, phenyl, 5–6 membered heteroaryl, or 5–6 membered heterocyclyl.

More preferred compounds of formula II are those having one or more, more preferably more than one, or most preferably all, of the features selected from the group consisting of:

(a) $T_nR^1$ is selected from optionally substituted phenyl, methyl, ethyl, propyl, cyclopropyl, cyclohexyl, $CH_2OCH_3$, $CH_2OH$, OH, $NH_2$, $NHCH_3$, NHAc, NHC(O)NHCH_3, or $CH_2NHCH_3$;

(b) Q is —CO—, —CONH—, —$SO_2$—, or —$SO_2NH$—;

(c) $R^2$ is —$(CH_2)_yR^4$, —$(CH_2)_yCH(R^4)_2$, or —$(CH_2)_yCH(R^7)CH(R^4)_2$, wherein $R^7$ is OH or $CH_2OH$; and (d) $R^4$ is —$CH_2OH$, —$(CH_2)_2OH$, isopropyl, —$CH_2NH_2$, —$(CH_2)_2NH_2$ or an optionally substituted group selected from pyrrolidin-1-yl, morpholin-4-yl, piperidin-1-yl, piperazin-1-yl, 4-methyl[1,4]diazepan-1-yl, 4-phenyl-piperazine-1-yl, pyridin-3-yl, pyridin-4-yl, imidazolyl, furan-2-yl, 1,2,3,4-tetrahydroisoquinoline, tetrahydrofuran-2-yl, cyclohexyl, phenyl, or benzyl.

Additional compounds of formula II include those of formula II':

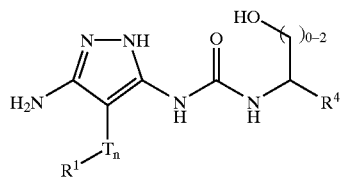

II'

Preferred $R^4$ groups of formula II' are optionally substituted 6-membered aryl, heteroaryl, and carbocyclic rings, such as phenyl, pyridyl, and cyclohexyl.

Preferred $T_nR^1$ groups of formula II' are as described above for formula II.

Preferred compounds of formula II' are those having one, and more preferably both, of the features selected from the group consisting of:

(a) $T_nR^1$ is hydrogen, $N(R^6)_2$, OH, 3–6 membered carbocyclyl, or an optionally substituted group selected from $C_{1-6}$ aliphatic or a 5–6 membered aryl or heteroaryl ring; and (b) $R^4$ is an optionally substituted 6-membered aryl, heteroaryl, or carbocyclic ring.

More preferred compounds of formula II' are those having one, and more preferably both, of the features selected from the group consisting of:

(a) $T_nR^1$ is selected from optionally substituted phenyl, methyl, ethyl, propyl, cyclopropyl, cyclohexyl, $CH_2OCH_3$, $CH_2OH$, OH, $NH_2$, $NHCH_3$, NHAc, NHC(O)NHCH_3, or $CH_2NHCH_3$; and (b) $R^4$ is cyclohexyl or an optionally substituted phenyl or pyridyl ring.

Additional compounds of formula II are further selected from those of formula II°:

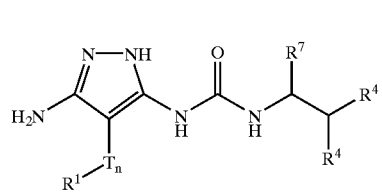

II°

Preferred $R^4$ groups of formula II° are R or $OR^6$. Examples of such groups include OH, $CH_2OH$, or optionally substituted 6-membered aryl, heteroaryl, and carbocyclic rings, such as phenyl, pyridyl, and cyclohexyl. Preferred $R^7$ groups of formula II° are R and $OR^6$, wherein R is an optionally substituted group selected from $C_{1-4}$ aliphatic, 3–6 membered heterocyclic, or a 5–6 membered aryl or heteroaryl ring. Preferred $R^7$ groups include phenyl, methyl, ethyl, OH, and $CH_2OH$.

Preferred $T_nR^1$ groups of formula II° are as described above for formula II.

Preferred compounds of formula II° are those having one, and more preferably both, of the features selected from the group consisting of:

(a) $T_nR^1$ is hydrogen, $N(R^6)_2$, OH, 3–6 membered carbocyclyl, or an optionally substituted group selected from $C_{1-6}$ aliphatic or a 5–6 membered aryl or heteroaryl ring; and (b) $R^4$ is R or $OR^6$, and $R^7$ is $R^6$ or $OR^6$.

More preferred compounds of formula II° are those having one, and more preferably both of the features selected from the group consisting of:

(a) $T_nR^1$ is selected from optionally substituted phenyl, methyl, ethyl, propyl, cyclopropyl, cyclohexyl, $CH_2OCH_3$, $CH_2OH$, OH, $NH_2$, $NHCH_3$, NHAc, NHC(O)NHCH_3, or $CH_2NHCH_3$; and (b) $R^4$ is OH, $CH_2OH$, phenyl, pyridyl, or cyclohexyl, and $R^7$ is methyl, ethyl, OH, or $CH_2OH$.

Exemplary structures of formula II, wherein n is 0, are set forth in Table 1 below.

TABLE 1

Compounds of formula II

| No. | R¹ | Q—R² |
|---|---|---|
| II-1 | 3-pyridyl | —C(=O)NH-CH₂-(2-methylpyridin-4-yl) |
| II-2 | piperidin-4-yl | —C(=O)NH-CH₂-(3-chloropyridin-4-yl) |
| II-3 | 1H-pyrazol-4-yl | —C(=O)NH-CH₂-(pyridin-4-yl) |
| II-4 | 3-pyridyl | —C(=O)NH-CH₂-(pyridin-4-yl) |
| II-5 | 3-pyridyl | —C(=O)N(CH₃)-CH₂-(pyridin-4-yl) |
| II-6 | isopropyl | —C(=O)NH-CH₂-(pyridin-4-yl) |
| II-7 | 1H-imidazol-4-yl | —C(=O)NH-CH₂-(pyridin-4-yl) |
| II-8 | 3-pyridyl | —C(=O)N(CH₃)-CH₂-(pyridin-4-yl) |

TABLE 1-continued
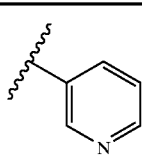
Compounds of formula II
| No. | R¹ | Q—R² |
|---|---|---|
| II-9 | 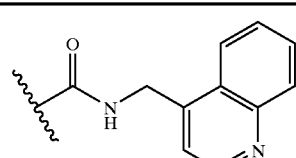 | 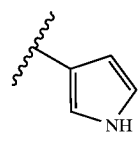 |
| II-10 | 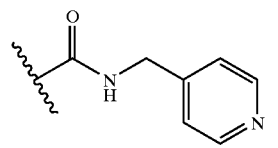 | 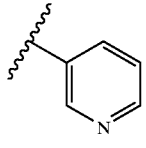 |
| II-11 | 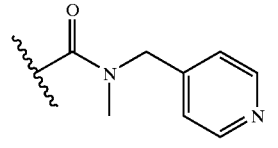 | 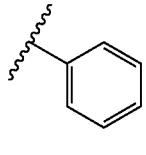 |
| II-12 | 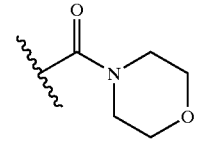 | 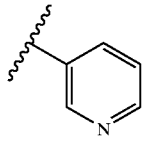 |
| II-13 | 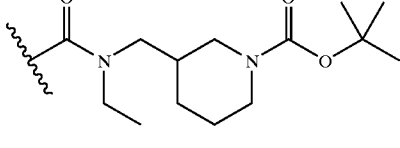 | 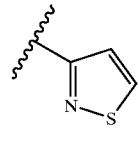 |
| II-14 | 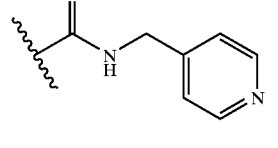 | 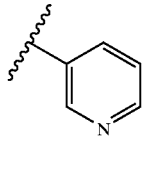 |
| II-15 | 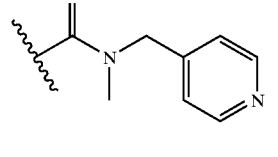 | 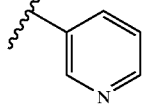 |
| II-16 | 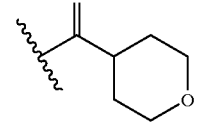 | |

TABLE 1-continued
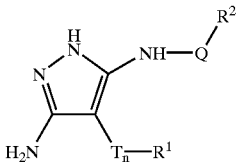
Compounds of formula II
| No. | R¹ | Q—R² |
|---|---|---|
| II-17 | 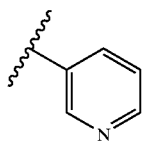 | 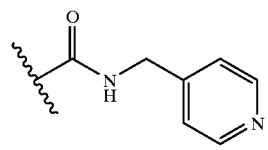 |
| II-18 | 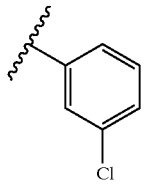 | 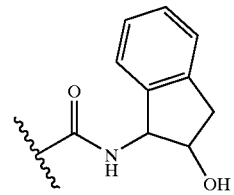 |
| II-19 | 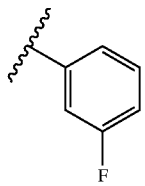 | 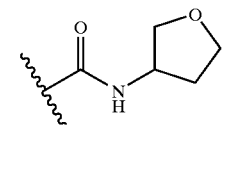 |
| II-20 | 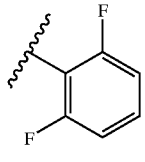 | 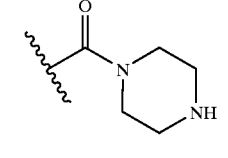 |
| II-21 | 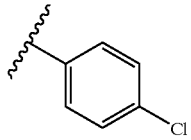 | 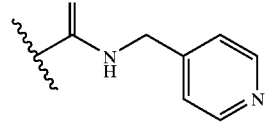 |
| II-22 | 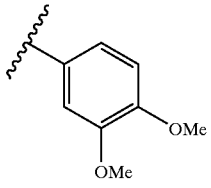 | 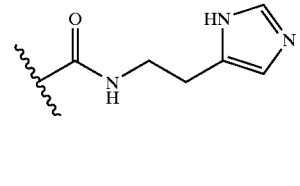 |
| II-23 | 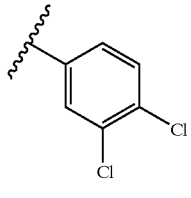 | 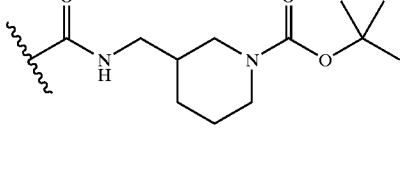 |

TABLE 1-continued
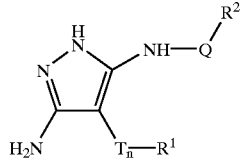
Compounds of formula II
| No. | R¹ | Q—R² |
|---|---|---|
| II-24 | 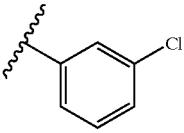 | 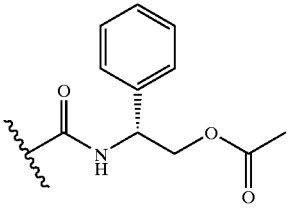 |
| II-25 | 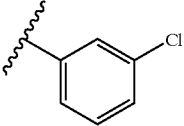 | 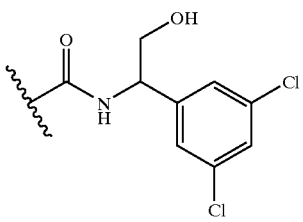 |
| II-26 | 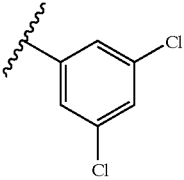 | 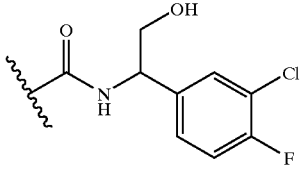 |
| II-27 | 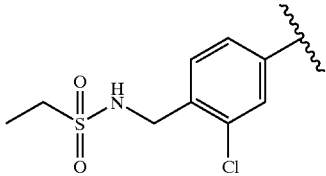 | 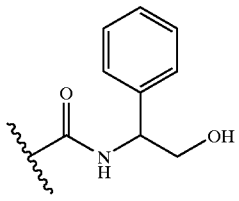 |
| II-28 | H | 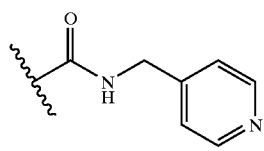 |

Exemplary structures of formula II, wherein T is —NH—, —NHNH—, —NHC(O)—, or —NHSO$_2$— and n is 1 are set forth in Table 2 below.

TABLE 2

Additional compounds of formula II

| No. | T | R$^1$ | Q—R$^2$ |
|---|---|---|---|
| II-29 | NH | 3-pyridyl | —C(O)NH-CH$_2$-(2-methylpyridin-4-yl) |
| II-30 | NH | 3-pyridyl | —C(O)NH-CH$_2$-(pyridin-4-yl) |
| II-31 | NH | piperidin-4-yl | —C(O)NH-CH$_2$-(3-chloropyridin-4-yl) |
| II-32 | NH | 1H-pyrazol-4-yl | —C(O)NH-CH$_2$-(pyridin-4-yl) |
| II-33 | NH | 3-pyridyl | —C(O)N(CH$_3$)-phenyl |
| II-34 | NH | isopropyl | —C(O)NH-CH$_2$-(pyridin-4-yl) |
| II-35 | NH | 1-methyl-1H-pyrazol-4-yl | —C(O)NH-CH$_2$-(pyridin-4-yl) |
| II-36 | NH | 3-pyridyl | —C(O)N(CH$_3$)-(1-methylpiperidin-4-yl) |
| II-37 | NH | CF$_3$ | —C(O)NH-CH$_2$-(pyridin-4-yl) |

TABLE 2-continued
Additional compounds of formula II
| No. | T | R¹ | Q—R² |
|---|---|---|---|
| II-38 | NH | 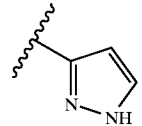 | 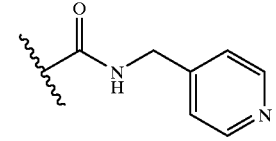 |
| II-39 | NH | 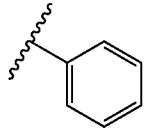 | 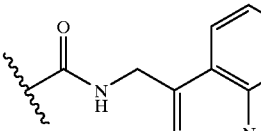 |
| II-40 | NH | 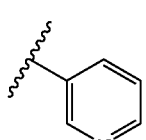 | 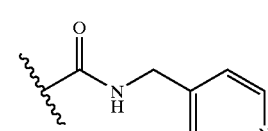 |
| II-41 | NH | 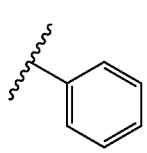 | 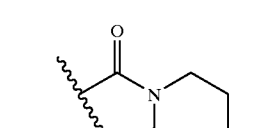 |
| II-42 | NH | 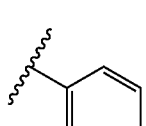 | 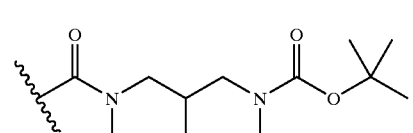 |
| II-43 | NH | 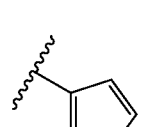 | 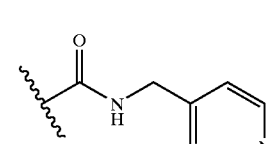 |
| II-44 | NH | 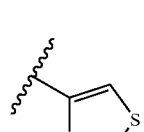 | 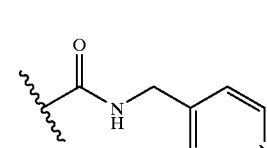 |
| II-45 | NHNH | 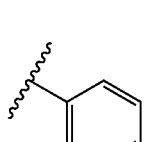 | 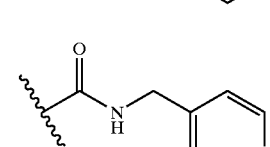 |
| II-46 | NHCO | 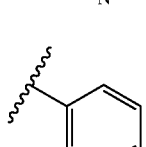 | 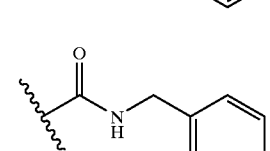 |

TABLE 2-continued
Additional compounds of formula II
| No. | T | R¹ | Q—R² |
|---|---|---|---|
| II-47 | NHSO₂ | 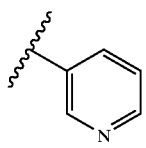 | 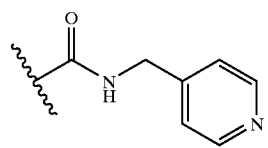 |
| II-48 | NH | 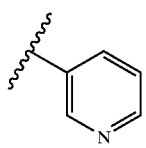 | 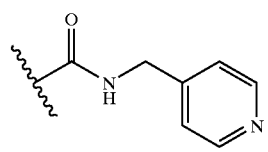 |
| II-49 | NH | 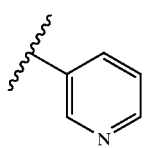 | 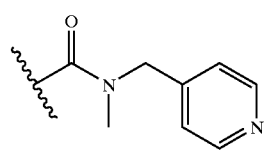 |
| II-50 | NH | 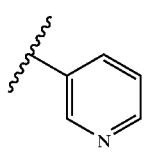 | 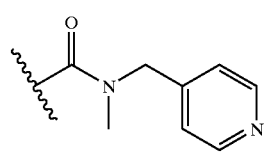 |
| II-51 | NH | 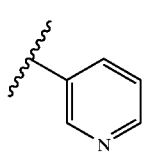 | 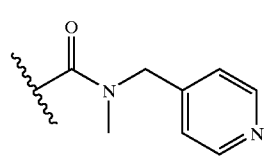 |
| II-52 | NH | 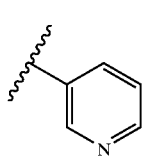 | 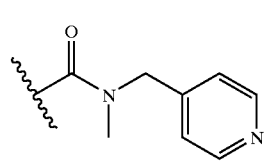 |
| II-53 | NH | 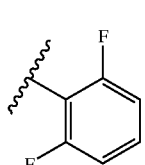 | 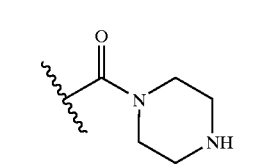 |
| II-54 | NH | 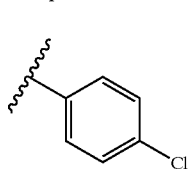 | 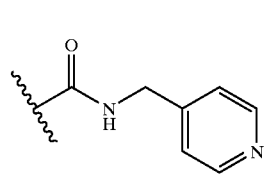 |
| II-55 | NH | 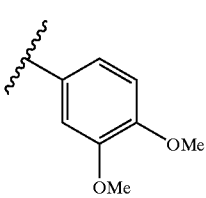 | 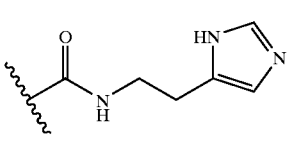 |

TABLE 2-continued

Additional compounds of formula II

| No. | T | R¹ | Q—R² |
|---|---|---|---|
| II-56 | NH | 3,4-dichlorophenyl | -C(O)NH-CH₂-(piperidin-3-yl)-N-Boc |
| II-57 | NH | 3-chlorophenyl | -C(O)NH-CH(Ph)-CH₂-O-C(O)CH₃ |
| II-58 | NH | 3-chlorophenyl | -C(O)NH-CH(3,5-dichlorophenyl)-CH₂OH |
| II-59 | NH | 3,5-dichlorophenyl | -C(O)NH-CH(3-chloro-4-fluorophenyl)-CH₂OH |
| II-60 | NH | 2-chloro-4-[(ethylsulfonylamino)methyl]phenyl | -C(O)NH-CH(Ph)-CH₂OH |

Additional preferred compounds, including those of formulae II' and II° are set forth in Table 3 below.

TABLE 3

Additional preferred compounds

| No. | $T_n$—R¹ | Q—R² |
|---|---|---|
| II-61 | 2-F-3-Cl-phenyl | -C(O)-N(CH₃)-CH(CH₃)-CH(OH)(Ph) |

TABLE 3-continued

Additional preferred compounds

| No. | T$_n$—R$^1$ | Q—R$^2$ |
|---|---|---|
| II-62 | methyl | (S)-NHC(O)—CH(CH$_2$OH)(Ph) |
| II-63 | methyl | (S)-NHC(O)—CH(CH$_2$CH$_2$OH)(Ph) |
| II-64 | Methyl | (R)-NHC(O)—CH(CH$_2$CH$_2$OH)(Ph) |
| II-65 | 3,5-dichlorophenyl | (S)-NHC(O)—CH(CH$_2$OH)(Ph) |
| II-66 | 3-F,5-CF$_3$-phenyl | (R)-NHC(O)—CH(CH$_2$OH)(Ph) |
| II-67 | Methyl | (R)-NHC(O)—CH(CH$_2$OH)(Ph) |
| II-68 | H | N(CH$_3$)C(O)— with CH(CH$_3$)CH(OH)(Ph) |
| II-69 | Methyl | NHC(O)—CH(CH$_2$OH)(CH$_2$CH(Me)$_2$) |

TABLE 3-continued

Additional preferred compounds

| No. | T$_n$—R$^1$ | Q—R$^2$ |
|---|---|---|
| II-70 | Methyl | (S)-2-amino-3-(1H-imidazol-4-yl)propan-1-ol amide |
| II-71 | Methyl | 2-amino-2-(3-chloro-4-fluorophenyl)ethanol amide |
| II-72 | Cyclohexyl | (R)-2-amino-2-phenylethanol amide |
| II-73 | Cyclopropyl | (R)-2-amino-2-phenylethanol amide |
| II-74 | Methyl | 2-amino-2-(3-fluoro-4-methylphenyl)ethanol amide |
| II-75 | Methyl | 2-amino-2-(3-trifluoromethylphenyl)ethanol amide |
| II-76 | CH$_2$OCH$_3$ | 2-amino-2-phenylethanol amide |
| II-77 | CH$_2$OH | 2-amino-2-phenylethanol amide |

TABLE 3-continued

Additional preferred compounds

| No. | $T_n$—$R^1$ | Q—$R^2$ |
|---|---|---|
| II-78 | Methyl | (structure: amide-NH-CH(CH₃)-CH(OH)-phenyl) |
| II-79 | Methyl | (structure: amide-NH-CH(CH₃)-CH(OH)-phenyl, different stereochemistry) |
| II-80 | Methyl | (structure: amide-NH-CH₂-CH(OH)-phenyl) |
| II-81 | Methyl | (structure: amide-NH-CH(CH₂OH)-CH(OH)-phenyl) |
| II-82 | Methyl | (structure: amide-NH-CH(CH₂OH)-CH(OH)-phenyl, different stereochemistry) |
| II-83 | H | (structure: amide-NH-CH(CH₃)-CH(OH)-phenyl) |
| II-84 | H | (structure: amide-NH-CH(CH₃)-CH(OH)-phenyl, different stereochemistry) |
| II-85 | H | (structure: amide-N(CH₃)-CH₂-CH(OH)-phenyl) |
| II-86 | H | (structure: amide-N(CH₃)-CH₂-CH(OH)-phenyl, different stereochemistry) |
| II-87 | H | (structure: amide-N(CH₃)-CH(CH₃)-CH(OH)-phenyl) |

TABLE 3-continued
Additional preferred compounds
| No. | T$_n$—R$^1$ | Q—R$^2$ |
|---|---|---|
| II-88 | H | 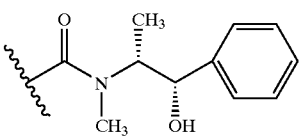 |
| II-89 | Methyl | 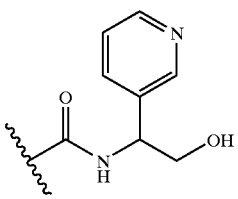 |
| II-90 | Methyl | 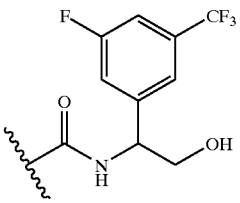 |
| II-91 | Methyl | 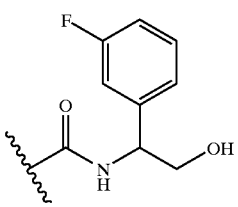 |
| II-92 | Methyl | 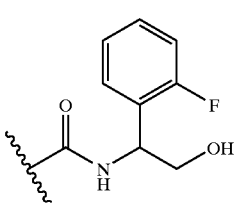 |
| II-93 | Methyl | 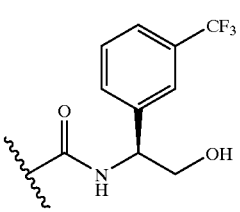 |
| II-94 | Methyl | 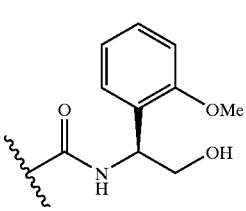 |

TABLE 3-continued
Additional preferred compounds
| No. | $T_n$—$R^1$ | Q—$R^2$ |
|---|---|---|
| II-95 | Methyl | 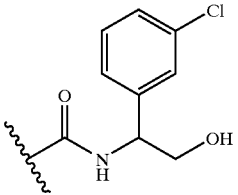 |
| II-96 | Methyl | 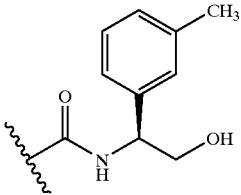 |
| II-97 | Methyl | 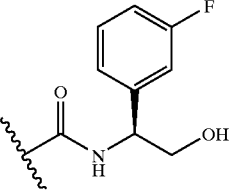 |
| II-98 | Methyl | 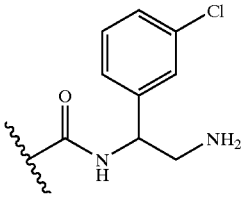 |
| II-99 | methyl | 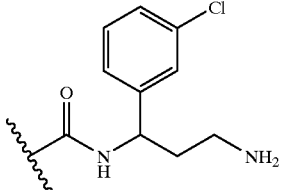 |
| II-100 | H | 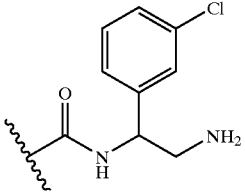 |
| II-101 | H | 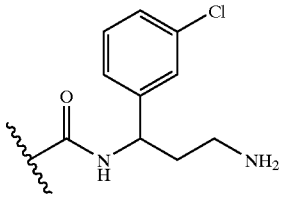 |

TABLE 3-continued
Additional preferred compounds
| No. | T$_n$—R$^1$ | Q—R$^2$ |
|---|---|---|
| II-102 | 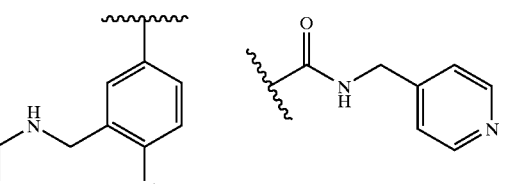 | 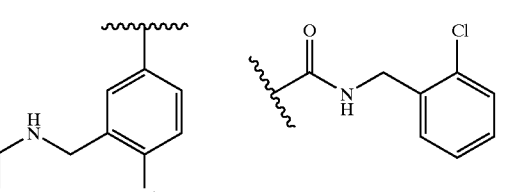 |
| II-103 | 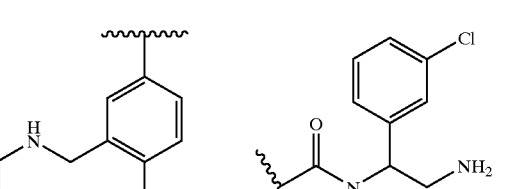 | 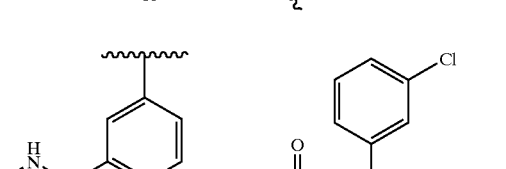 |
| II-104 | 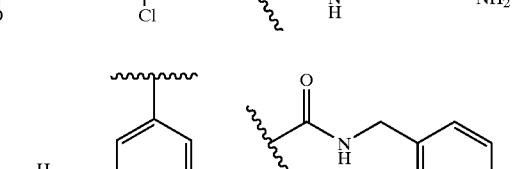 | 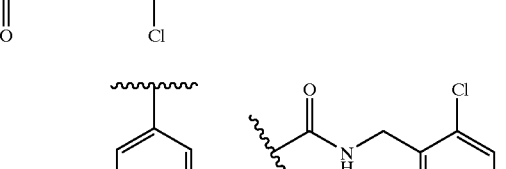 |
| II-105 | 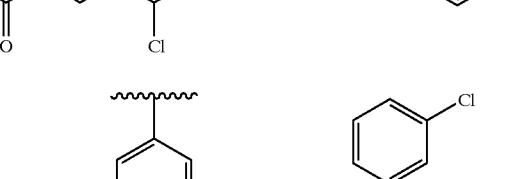 | 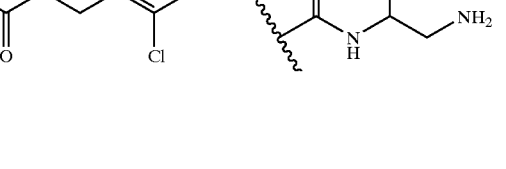 |
| II-106 | 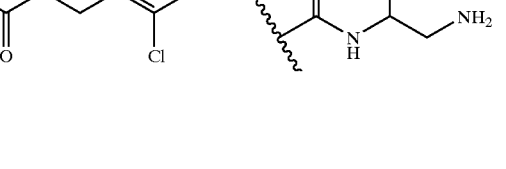 | 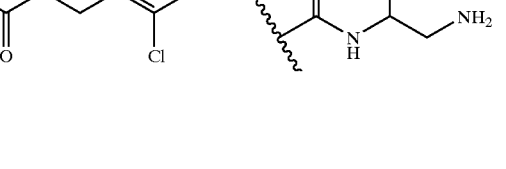 |
| II-107 | 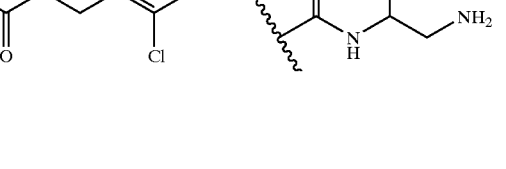 | 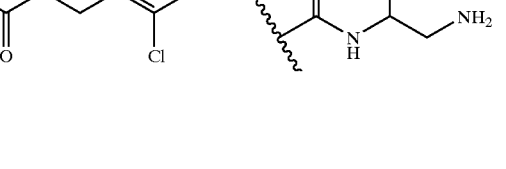 |
| II-108 | 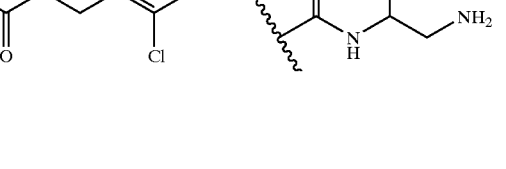 | 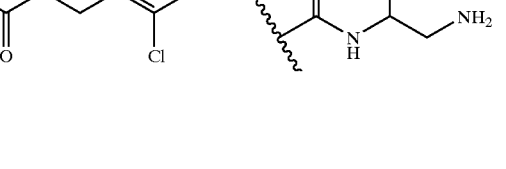 |

TABLE 3-continued

Additional preferred compounds

| No. | $T_n$—$R^1$ | Q—$R^2$ |
|---|---|---|
| II-109 | 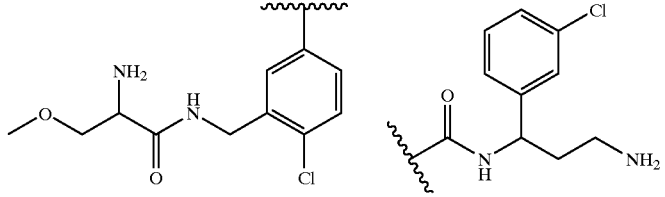 |  |

The present compounds may be prepared in general by methods known to those skilled in the art for analogous compounds, as illustrated by the general Schemes I and II shown below.

Scheme I

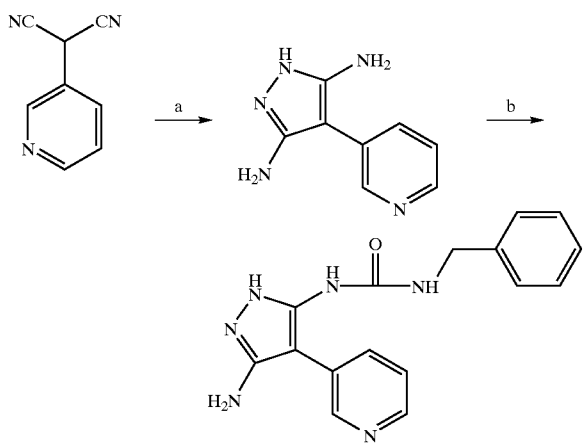

Reagents and conditions: (a) hydrazine, ethanol (EtOH), reflux for 18 hours; (b) benzyl isocyanate, N,N-dimethylformamide (DMF), 0° C., 3 hours.

Scheme II

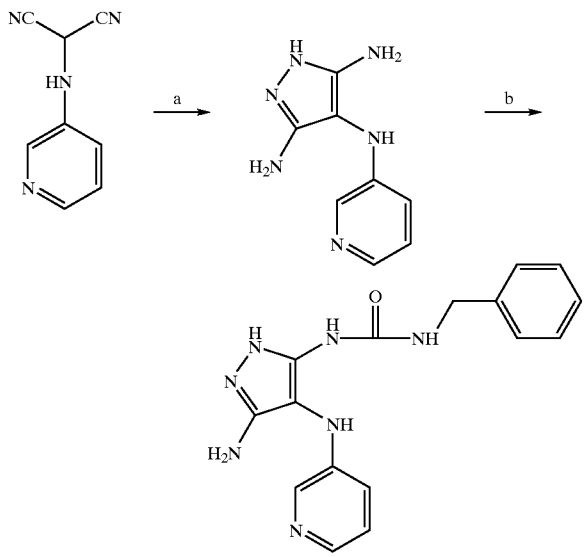

Reagents and conditions: (a) hydrazine, EtOH, reflux for 18 hours; (b) benzyl isocyanate, DMF 0° C., 3 hours.

Schemes I and II above show general synthetic routes that were used for preparing the compounds of this invention when $R^1$ is an optionally substituted pyridyl group. Scheme I exemplifies the preparation of a compound in which n is 0 and scheme II exemplifies the preparation of a compound in which n is 1. one having ordinary skill in the art may synthesize other compounds of this invention following the teachings of the specification using reagents that are readily synthesized or commercially available.

The activity of a compound utilized in this invention as an inhibitor of ERK, may be assayed in vitro, in vivo or in a cell line according to methods known in the art. In vitro assays include assays that determine inhibition of either the phosphorylation activity or ATPase activity of activated ERK. Alternate in vitro assays quantitate the ability of the inhibitor to bind to ERK. Inhibitor binding may be measured by radiolabelling the inhibitor prior to binding, isolating the inhibitor/ERK complex and determining the amount of radiolabel bound. Alternatively, inhibitor binding may be determined by running a competition experiment where new inhibitors are incubated with ERK bound to known radioligands. Detailed conditions for assaying a compound utilized in this invention as an inhibitor of ERK kinase are set forth in the Examples below.

According to another embodiment, the invention provides a composition comprising a compound of this invention or a pharmaceutically acceptable derivative thereof and a pharmaceutically acceptable carrier, adjuvant, or vehicle. The amount of compound in the compositions of this invention is such that is effective to detectably inhibit a protein kinase, particularly ERK in a biological sample or in a patient. Preferably the composition of this invention is formulated for administration to a patient in need of such composition. Most preferably, the composition of this invention is formulated for oral administration to a patient.

The term "patient", as used herein, means an animal, preferably a mammal, and most preferably a human.

The term "pharmaceutically acceptable carrier, adjuvant, or vehicle" refers to a non-toxic carrier, adjuvant, or vehicle that does not destroy the pharmacological activity of the compound with which it is formulated. Pharmaceutically acceptable carriers, adjuvants or vehicles that may be used in the compositions of this invention include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

The term "detectably inhibit", as used herein means a measurable change in ERK activity between a sample comprising said composition and an ERK kinase and an equivalent sample comprising ERK kinase in the absence of said composition. According to a preferred embodiment, inhibition of kinase activity by a compound according to the present invention is greater than 10% compared to the kinase activity in the absence of the compound. Preferably, inhibition is greater than 20%, 30%, or 40%, and even more preferably greater than 50%, 60%, 70%, 80%, or 90%.

A "pharmaceutically acceptable derivative"means any non-toxic salt, ester, salt of an ester or other derivative of a compound of this invention that, upon administration to a recipient, is capable of providing, either directly or indirectly, a compound of this invention or an inhibitorily active metabolite or residue thereof.

Pharmaceutically acceptable salts of the compounds of this invention include those derived from pharmaceutically acceptable inorganic and organic acids and bases. Examples of suitable acid salts include acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, formate, fumarate, glucoheptanoate, glycerophosphate, glycolate, hemisulfate, heptanoate, hexanoate, hydrochloride, hydrobromide, hydroiodide, 2-hydroxyethanesulfonate, lactate, maleate, malonate, methanesulfonate, 2-naphthalenesulfonate, nicotinate, nitrate, oxalate, palmoate, pectinate, persulfate, 3-phenylpropionate, phosphate, picrate, pivalate, propionate, salicylate, succinate, sulfate, tartrate, thiocyanate, tosylate and undecanoate. Other acids, such as oxalic, while not in themselves pharmaceutically acceptable, may be employed in the preparation of salts useful as intermediates in obtaining the compounds of the invention and their pharmaceutically acceptable acid addition salts.

Salts derived from appropriate bases include alkali metal (e.g., sodium and potassium), alkaline earth metal (e.g., magnesium), ammonium and $N^+(C_{1-4}\ alkyl)_4$ salts. This invention also envisions the quaternization of any basic nitrogen-containing groups of the compounds disclosed herein. Water or oil-soluble or dispersible products may be obtained by such quaternization.

The compositions of the present invention may be administered orally, parenterally, by inhalation spray, topically, rectally, nasally, buccally, vaginally or via an implanted reservoir. The term "parenteral" as used herein includes subcutaneous, intravenous, intramuscular, intra-articular, intra-synovial, intrasternal, intrathecal, intrahepatic, intralesional and intracranial injection or infusion techniques. Preferably, the compositions are administered orally, intraperitoneally or intravenously. Sterile injectable forms of the compositions of this invention may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally-acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium.

For this purpose, any bland fixed oil may be employed including synthetic mono- or di-glycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as carboxymethyl cellulose or similar dispersing agents that are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms may also be used for the purposes of formulation.

The pharmaceutically acceptable compositions of this invention may be orally administered in any orally acceptable dosage form including, but not limited to, capsules, tablets, aqueous suspensions or solutions. In the case of tablets for oral use, carriers commonly used include lactose and corn starch. Lubricating agents, such as magnesium stearate, are also typically added. For oral administration in a capsule form, useful diluents include lactose and dried cornstarch. When aqueous suspensions are required for oral use, the active ingredient is combined with emulsifying and suspending agents. If desired, certain sweetening, flavoring or coloring agents may also be added.

Alternatively, the pharmaceutically acceptable compositions of this invention may be administered in the form of suppositories for rectal administration. These can be prepared by mixing the agent with a suitable non-irritating excipient that is solid at room temperature but liquid at rectal temperature and therefore will melt in the rectum to release the drug. Such materials include cocoa butter, beeswax and polyethylene glycols.

The pharmaceutically acceptable compositions of this invention may also be administered topically, especially when the target of treatment includes areas or organs readily accessible by topical application, including diseases of the eye, the skin, or the lower intestinal tract. Suitable topical formulations are readily prepared for each of these areas or organs.

Topical application for the lower intestinal tract can be effected in a rectal suppository formulation (see above) or in a suitable enema formulation. Topically-transdermal patches may also be used.

For topical applications, the pharmaceutically acceptable compositions may be formulated in a suitable ointment containing the active component suspended or dissolved in one or more carriers. Carriers for topical administration of the compounds of this invention include, but are not limited to, mineral oil, liquid petrolatum, white petrolatum, propylene glycol, polyoxyethylene, polyoxypropylene compound, emulsifying wax and water. Alternatively, the pharmaceutically acceptable compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water.

For ophthalmic use, the pharmaceutically acceptable compositions may be formulated as micronized suspensions in isotonic, pH adjusted sterile saline, or, preferably, as solutions in isotonic, pH adjusted sterile saline, either with or without a preservative such as benzylalkonium chloride.

Alternatively, for ophthalmic uses, the pharmaceutically acceptable compositions may be formulated in an ointment such as petrolatum.

The pharmaceutically acceptable compositions of this invention may also be administered by nasal aerosol or inhalation. Such compositions are prepared according to techniques well-known in the art of pharmaceutical formulation and may be prepared as solutions in saline, employing benzyl alcohol or other.suitable preservatives, absorption promoters to enhance bioavailability, fluorocarbons, and/or other conventional solubilizing or dispersing agents.

Most preferably, the pharmaceutically acceptable compositions of this invention are formulated for oral administration.

The amount of the compounds of the present invention that may be combined with the carrier materials to produce a composition in a single dosage form will vary depending upon the host treated, the particular mode of administration. Preferably, the compositions should be formulated so that a dosage of between 0.01–100 mg/kg body weight/day of the inhibitor can be administered to a patient receiving these compositions.

It should also be understood that a specific dosage and treatment regimen for any particular patient will depend upon a variety of factors, including the activity of the specific compound employed, the age, body weight, general health, sex, diet, time of administration, rate of excretion, drug combination, and the judgment of the treating physician and the severity of the particular disease being treated. The amount of a compound of the present invention in the composition will also depend upon the particular compound in the composition.

Depending upon the particular condition, or disease, to be treated or prevented, additional therapeutic agents, which are normally administered to treat or prevent that condition, may also be present in the compositions of this invention. As used herein, additional therapeutic agents that are normally administered to treat or prevent a particular disease, or condition, are known as "appropriate for the disease, or condition, being treated".

For example, chemotherapeutic agents or other antiproliferative agents may be combined with the compounds of this invention to treat proliferative diseases and cancer. Examples of known chemotherapeutic agents include, but are not limited to, Gleevec™, adriamycin, dexamethasone, vincristine, cyclophosphamide, fluorouracil, topotecan, taxol, interferons, and platinum derivatives.

Other examples of agents the compounds of this invention may also be combined with include, without limitation, anti-inflammatory agents such as corticosteroids, TNF blockers, IL-1 RA, azathioprine, cyclophosphamide, and sulfasalazine; immunomodulatory and immunosuppressive agents such as cyclosporin, tacrolimus, rapamycin, mycophenolate mofetil, interferons, corticosteroids, cyclophophamide, azathioprine, and sulfasalazine; neurotrophic factors such as acetylcholinesterase inhibitors, MAO inhibitors, interferons, anti-convulsants, ion channel blockers, riluzole, and anti-Parkinsonian agents; agents for treating cardiovascular disease such as beta-blockers, ACE inhibitors, diuretics, nitrates, calcium channel blockers, and statins; agents for treating liver disease such as corticosteroids, cholestyramine, interferons, and anti-viral agents; agents for treating blood disorders such as corticosteroids, anti-leukemic agents, and growth factors; agents for treating diabetes such as insulin, insulin analogues, alpha glucosidase inhibitors, biguanides, and insulin sensitizers; and agents for treating immunodeficiency disorders such as gamma globulin.

The amount of additional therapeutic agent present in the compositions of this invention will be no more than the amount that would normally be administered in a composition comprising that therapeutic agent as the only active agent. Preferably the amount of additional therapeutic agent in the presently disclosed compositions will range from about 50% to 100% of the amount normally present in a composition comprising that agent as the only therapeutically active agent.

According to another embodiment, the invention relates to a method of inhibiting ERK kinase activity in a biological sample comprising the step of contacting said biological sample with a compound of this invention, or a pharmaceutically acceptable composition comprising said compound.

The term "biological sample", as used herein, includes, without limitation, cell cultures or extracts thereof; biopsied material obtained from a mammal or extracts thereof; and blood, saliva, urine, feces, semen, tears, or other body fluids or extracts thereof.

Inhibition of ERK kinase activity in a biological sample is useful for a variety of purposes that are known to one of skill in the art. Examples of such purposes include, but are not limited to, blood transfusion, organ-transplantation, biological specimen storage, and biological assays.

According to another embodiment, the invention provides a method for treating or lessening the severity of an ERK-mediated disease or condition in a patient comprising the step of administering to said patient a pharmaceutically acceptable composition according to the present invention.

The term "ERK-mediated condition" or "disease", as used herein, means any disease or other deleterious condition in which ERK is known to play a role. The term "ERK-mediated condition" or "disease" also means those diseases or conditions that are alleviated by treatment with an ERK inhibitor. Such conditions include, without limitation, cancer, stroke, diabetes, hepatomegaly, cardiovascular disease including cardiomegaly, Alzheimer's disease, cystic fibrosis, viral disease, autoimmune diseases, atherosclerosis, restenosis, psoriasis, allergic disorders including asthma, inflammation, neurological disorders and hormone-related diseases. The term "cancer" includes, but is not limited to the following cancers: breast, ovary, cervix, prostate, testis, genitourinary tract, esophagus, larynx, glioblastoma, neuroblastoma, stomach, skin, keratoacanthoma, lung, epidermoid carcinoma, large cell carcinoma, small cell carcinoma, lung adenocarcinoma, bone, colon, adenoma, pancreas, adenocarcinoma, thyroid, follicular carcinoma, undifferentiated carcinoma, papillary carcinoma, seminoma, melanoma, sarcoma, bladder carcinoma, liver carcinoma and biliary passages, kidney carcinoma, myeloid disorders, lymphoid disorders, Hodgkin's, hairy cells, buccal cavity and pharynx (oral), lip, tongue, mouth, pharynx, small intestine, colon-rectum, large intestine, rectum, brain and central nervous system, and leukemia.

Compounds of the present invention are also useful as inhibitors of related kinases to ERK. The term "related kinases" refer to protein kinases having residues which are similar to those residues which line the ERK binding site. Without wishing to be bound by theory, applicants speculate that this inhibitory activity is due to the close structural similarity between the active sites of ERK and related kinases. The alignment of the ERK sequence with other kinases can be derived from common software programs such as the "bestfit" program available from Genetics Computer Group. This program uses the local homology algorithm described by Smith and Waterman in *Advances in Applied Mathematics* 2; 482 (1981).

Related kinases inhibited by the compounds of this invention would contain residues, identified by the above standard protein sequence alignment software, corresponding to the ERK residues: I31, E33, G34, A35, Y36, G37, M38, V39, A52, K54, R$^{67}$, T68, E71, L75, I84, I86, I103, Q105, D106, L107, M108, E109, D111, K114, D149, K151, S153, N154, L156, C166, and D167, with a similarity score of 80% or greater. In a more preferred embodiment the similarity score is 85%, more preferably 90%, even more preferably 95%, 96%, 97% or 98%. The similarity score may be determined using standard amino acid substitution tables such as those described by Dayhoff (Dayhoff, M. O., et al, *Atlas of Protein Sequence and Structure*, 1979) and Blosom-Henikoff (Blosum-Henikoff, S and Henikoff, J. G., *PNAS*, 1992, 89:10915–10919). The term "related kinases" also includes those containing residues with a similarity score of 80% or greater to the following ERK residues: I31, G37, A52, I103, E109, and N154. In a more preferred embodiment the similarity score is 85%, more preferably 90%, even more preferably 95%, 96%, 97% or 98%.

The present method is especially useful for treating a disease that is alleviated by the use of an inhibitor of ERK or related kinases. As used herein, unless otherwise indicated, the term "ERK" refers to all isoforms of the ERK enzyme including, but not limited to, ERK1, ERK2, ERK3, ERK4, ERK5, ERK6, and ERK7.

In an alternate embodiment, the methods of this invention that utilize compositions that do not contain an additional therapeutic agent, comprise the additional step of separately administering to said patient an additional therapeutic agent. When these additional therapeutic agents are administered separately they may be administered to the patient prior to, sequentially with or following administration of the compositions of this invention.

The compounds of this invention or pharmaceutically acceptable compositions thereof may also be incorporated into compositions for coating an implantable medical device, such as prostheses, artificial valves, vascular grafts, stents and catheters. Vascular stents, for example, have been used to overcome restenosis (re-narrowing of the vessel wall after injury). However, patients using stents or other implantable devices risk clot formation or platelet activation. These unwanted effects may be prevented or mitigated by pre-coating the device with a pharmaceutically acceptable composition comprising a kinase inhibitor. Suitable coatings and the general preparation of coated implantable devices are described in U.S. Pat. Nos. 6,099,562; 5,886,026; and 5,304,121. The coatings are typically biocompatible polymeric materials such as a hydrogel polymer, polymethyldisiloxane, polycaprolactone, polyethylene glycol, polylactic acid, ethylene vinyl acetate, and mixtures thereof. The coatings may be further covered by a suitable topcoat of fluorosilicone, polysaccharides, polyethylene glycol, phospholipids or combinations thereof to impart controlled release characteristics in the composition. Implantable devices coated with a compound of this invention are another embodiment of the present invention.

In order that the invention described herein may be more fully understood, the following examples are set forth. It should be understood that these examples are for illustrative purposes only and are not to be construed as limiting this invention in any manner.

EXAMPLES

Example 1

ERK Inhibition Assay

The ADP produced from ATP by the human recombinant ERK2 kinase-catalyzed phosphorylation of ERKtide peptide (ATGPLSPGPFGRR)substrate is quantified using a spectrometric coupled enzyme assay (Fox et al., (1998) *Protein Sci.* 7, 2249). In this assay one molecule of NADH is oxidized to NAD for every molecule of ADP produced in the kinase reaction. The disappearance of NADH can be conveniently followed at 340 nm.

The final concentrations of the assay components are: 0.1 M HEPES, pH 7.6, 10 mM $MgCl_2$, 2 mM DTT, 150 μM ERKtide and 15 nM of recombinant human ERK2 kinase. Final concentrations of the components of the coupled enzyme system are 2.5 mM phosphoenolpyruvate, 200 μM NADH, 30 μg/ml pyruvate kinase and 10 μg/ml lactate dehydrogenase.

All reaction components with the exception of ATP are pre-mixed and aliquoted into assay plate wells. Inhibitors dissolved in DMSO are added to the wells to give a final DMSO concentration of 2.5%. The assay plate is incubated at 30° C. for 10 min before initiating the reaction with 65 μM ATP. The absorbance change with time (the rate of the reaction) is monitored at 340 nm on a molecular devices plate reader. The rate data as a function of inhibitor concentration is fitted to the competitive inhibition kinetics model to calculate $K_i$.

Example 2

ERK Inhibition Cell Proliferation Assay

Compounds may be assayed for the inhibition of ERK2 by a cell proliferation assay. In this assay, a complete media is prepared by adding 10% fetal bovine serum and penicillin/streptomycin solution to RPMI 1640 medium (JRH Biosciences). Colon cancer cells (HT-29 cell line) are added to each of 84 wells of a 96 well plate at a seeding density of 10,000 cells/well/150 μL. The cells are allowed to attach to the plate by incubating at 37° C. for 2 hours. A solution of test compound is prepared in complete media by serial dilution to obtain the following concentrations: 20 μM, 6.7 μM, 2.2 μM, 0.74 μM, 0.25 μM, and 0.08 μM. The test compound solution (50 μL) is added to each of 72 cell-containing wells. To the 12 remaining cell-containing wells, only complete media (200 μL) is added to form a control group in order to measure maximal proliferation. To the remaining 12 empty wells, complete media is added to form a vehicle control group in order to measure background. The plates are incubated at 37° C. for 3 days. A stock solution of $^3$H-thymidine (1 mCi/mL, New England Nuclear, Boston, Mass.) is diluted to 20 μCi/mL in RPMI medium then 20 μL of this solution is added to each well. The plates are further incubated at 37° C. for 8 hours then harvested and analyzed for $^3$H-thymidine uptake using a liquid scintillation counter.

While we have described a number of embodiments of this invention, it is apparent that these basic examples may be altered to provide other embodiments, which utilize the compounds and methods of this invention. Therefore, it will be appreciated that the scope of this invention is to be defined by the appended claims rather than by the specific embodiments, which have been represented by way of example.

I claim:
1. A compound of formula I:

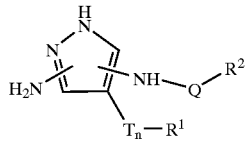

or a pharmaceutically acceptable salt or derivative thereof, wherein:
T is selected from —NH—, —NHC(O)—, —NHC(O)O—, —NHC(O)NR—, —NHC(O)NH—, —NHSO$_2$—, —NHSO$_2$NR—, —NHSO$_2$NH—, —NHNR—, —NHNH—, —NHNRC(O)—, —NHNHC(O)—, —NHNRSO$_2$—, or —NHNHSO$_2$—;
n is 0 or 1;
each R is independently selected from an optionally substituted group selected from C$_{1-6}$ aliphatic, C$_{6-10}$ aryl, heteroaryl having 5–10 ring atoms, and heterocyclyl having 3–10 ring atoms;
R$^1$ is selected from hydrogen, —CN, halogen, —N(R$^6$)$_2$, —OR, —OH, or —R;
R$^2$ is selected from —(CH$_2$)$_y$R$^4$, —(CH$_2$)$_y$CH(R$^4$)$_2$, —(CH$_2$)$_y$CH(R$^7$)CH(R$^4$)$_2$, —N(R$^3$)$_2$, or —NR$^3$(CH$_2$)$_y$N(R$^3$)$_2$;
Q is selected from —C(O)C(O)—, —C(O)CH$_2$C(O)—, —C(O)NR—, —SO$_2$NR$^6$—, —NR$^6$—, —NRC(O)—, —NRSO$_2$—, —NRC(O)O—, —NRC(O)NR$^6$—, or —C(O)NR$^6$—;
y is 0–6;
each R$^3$ is independently selected from R, R$^6$, —COR$^6$, —CO$_2$R, —CON(R$^6$)$_2$, —SO$_2$R$^6$, —(CH$_2$)$_y$R$^4$, or —(CH$_2$)$_y$CH(R$^4$)$_2$;
each R$^4$ is independently selected from —R, —OR, —CO$_2$R, —(CH$_2$)$_y$N(R$^6$)$_2$, —N(R$^6$)$_2$, —OR$^6$, —SR$^6$, —NR$^6$COR$^6$, —NR$^6$CON(R$^6$)$_2$, —C(O)N(R$^6$)$_2$, —SO$_2$R$^6$, —NR$^6$SO$_2$R$^6$, —C(O)R$^6$, —CN, or —SO$_2$N(R$^6$)$_2$;
each R$^6$ is independently selected from hydrogen or an optionally substituted C$_{1-6}$ aliphatic group, or two R$^6$ on the same nitrogen are taken together with the nitrogen to form a 5–8 membered heterocyclyl or heteroaryl ring;
each R$^7$ is selected from —R$^6$—(CH$_2$)$_w$OR$^6$, —(CH$_2$)$_w$N(R$^3$)$_2$, or —(CH$_2$)$_w$SR$^6$; and
each w is independently selected from 0–4;

2. The compound according to claim 1, wherein said compound is of formula II:

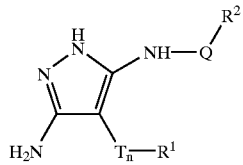

or a pharmaceutical acceptable salt or derivative thereof.
3. The compound according to claim 2 wherein said compound has one or more features selected from the group consisting of: (a) T$_n$R$^1$ is hydrogen, amino, OH, 3–6 membered carbocyclyl, or an optionally substituted group selected from C$_{1-6}$ aliphatic or a 5–6 membered aryl or heteroaryl ring; (b) Q is —CONH—, —SO$_2$NH—, —OC(O)NH—, —C(O)ONH—, or —CONHNH—; (c) R$^2$ is —NR$^3$(CH$_2$)$_y$N(R$^3$)$_2$, —(CH$_2$)$_y$R$^4$, —(CH$_2$)$_y$CH(R$^4$)$_2$, or —(CH$_2$)$_y$CH(R$^7$)CH(R$^4$)$_2$; (d) R$^3$ is R, R$^6$, or —(CH$_2$)$_y$CH(R$^4$)$_2$; and (e) R$^4$ is an optionally substituted group selected from C$_{1-6}$ aliphatic, phenyl, 5–6 membered heteroaryl, or 5–6 membered heterocyclyl.

4. The compound according to claim 3 wherein: (a) T$_n$R$^1$ is hydrogen, amino, OH, 3–6 membered carbocyclyl, or an optionally substituted group selected from C$_{1-6}$ aliphatic or a 5–6 membered aryl or heteroaryl ring; (b) Q is —CONH—, —SO$_2$NH—, —OC(O)NH—, —C(O)ONH—, or —CONHNH—; (c) R$^2$ is —NR$^3$(CH$_2$)$_y$N(R$^3$)$_2$, —(CH$_2$)$_y$R$^4$, —(CH$_2$)$_y$CH(R$^4$)$_2$, or —(CH$_2$)$_y$CH(R$^7$)CH(R$^4$)$_2$; (d) R$^3$ is R, R$^6$, or —(CH$_2$)$_y$CH(R$^4$)$_2$; and (e) R$^4$ is an optionally substituted group selected from C$_{1-6}$ aliphatic, phenyl, 5–6 membered heteroaryl, or 5–6 membered heterocyclyl.

5. The compound according to claim 4 wherein: (a) T$_n$R$^1$ is optionally substituted phenyl, methyl, ethyl, propyl, cyclopropyl, cyclohexyl, CH$_2$OCH$_3$, CH$_2$OH, OH, NH$_2$, NHCH$_3$, NHAc, NHC(O)NHCH$_3$, or CH$_2$NHCH$_3$; (b) Q is —CONH—, or —SO$_2$NH—; (c) R$^2$ is —(CH$_2$)$_y$R$^4$, —(CH$_2$)$_y$CH(R$^4$)$_2$, or —(CH$_2$)$_y$CH(R$^7$)CH(R$^4$)$_2$, wherein R$^7$ is OH or CH$_2$OH; and (d) R$^4$ is —CH$_2$OH, —(CH$_2$)$_2$OH, isopropyl, —CH$_2$NH$_2$, and —(CH$_2$)$_2$NH$_2$ or an optionally substituted group selected from pyrrolidin-1-yl, morpholin-4-yl, piperidin-1-yl, piperazin-1-yl, 4-methyl[1,4]diazepan-1-yl, 4-phenylpiperazine-1-yl, pyridin-3-yl, pyridin-4-yl, imidazolyl, furan-2-yl, 1,2,3,4-tetrahydroisoquinoline, tetrahydrofuran-2-yl, cyclohexyl, phenyl, or benzyl.

6. The compound according to claim 2 wherein said compound is selected from the following:

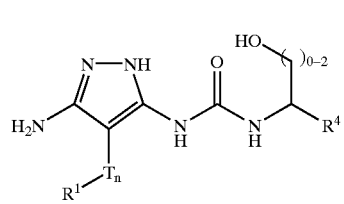

or a pharmaceutically acceptable salt or derivative thereof.

7. The compound according to claim 6 wherein said compound has one or more features selected from the group consisting of: (a) T$_n$R$^1$ is hydrogen, N(R$^3$)$_2$, OH, 3–6 membered carbocyclyl, or an optionally substituted group selected from C$_{1-6}$ aliphatic or a 5–6 membered aryl or heteroaryl ring; and (b) R$^4$ is an optionally substituted 6-membered aryl, heteroaryl, or carbocyclic ring.

8. The compound according to claim 7 wherein: (a) T$_n$R$^1$ is selected from optionally substituted phenyl, methyl, ethyl, propyl, cyclopropyl, cyclohexyl, CH$_2$OCH$_3$, CH$_2$OH, OH, NH$_2$, NHCH$_3$, NHAc, NHC(O)NHCH$_3$, or CH$_2$NHCH$_3$; and (b) R$^4$ is cyclohexyl or an optionally substituted phenyl or pyridyl ring.

9. The compound according to claim 2 wherein said compound is selected from the following:

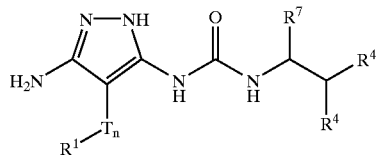

or a pharmaceutically acceptable salt or derivative thereof.

10. The compound according to claim 9 wherein said compound has one or more features selected from the group consisting of: (a) $T_nR^1$ is hydrogen, $N(R^3)_2$, OH, 3–6 membered carbocyclyl, or an optionally substituted group selected from $C_{1-6}$ aliphatic or a 5–6 membered aryl or heteroaryl ring; and (b) $R^4$ is R or $OR^6$, and $R^7$ is $R^6$ or $OR^6$.

11. The compound according to claim 10 wherein: (a) $T_nR^1$ is selected from optionally substituted phenyl, methyl, ethyl, propyl, cyclopropyl, cyclohexyl, $CH_2OCH_3$, $CH_2OH$, OH, $NH_2$, $NHCH_3$, NHAc, $NHC(O)NHCH_3$, or $CH_2NHCH_3$; and (b) $R^4$ is OH, $CH_2OH$, phenyl, pyridyl, or cyclohexyl, and $R^7$ is methyl, ethyl, OH, or $CH_2OH$.

12. The compound according to claim 2 wherein n is 0 and wherein said compound is selected from any one of the following compounds:

| No. | $R^1$ | $Q—R^2$ |
|---|---|---|
| II-1 | 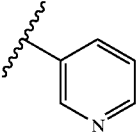 | 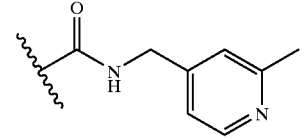 |
| II-2 | 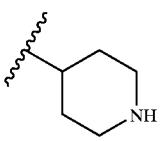 | 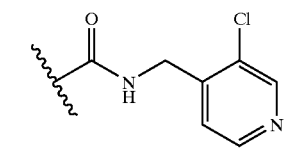 |
| II-3 | 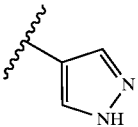 | 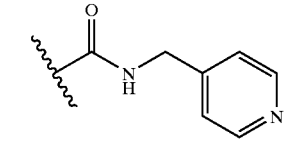 |
| II-4 | 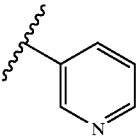 | 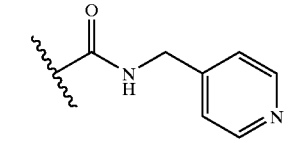 |
| II-5 | 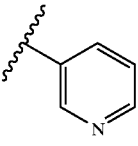 | 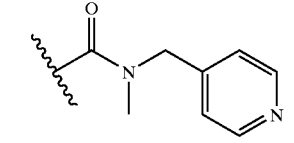 |
| II-6 | 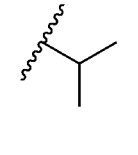 | 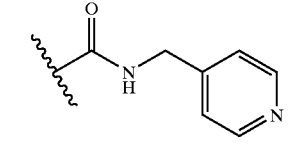 |
| II-7 | 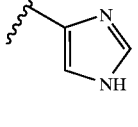 | 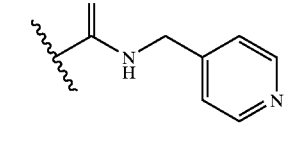 |

-continued

| No. | R¹ | Q—R² |
|---|---|---|
| II-8 | 3-pyridyl | -C(O)-N(CH₃)-CH₂-(4-pyridyl) |
| II-9 | 3-pyridyl | -C(O)-NH-CH₂-(quinolin-4-yl) |
| II-10 | 1H-pyrrol-3-yl | -C(O)-NH-CH₂-(4-pyridyl) |
| II-11 | 3-pyridyl | -C(O)-N(CH₃)-CH₂-(4-pyridyl) |
| II-13 | 3-pyridyl | -C(O)-N(Et)-CH₂-(1-Boc-piperidin-3-yl) |
| II-14 | isothiazol-3-yl | -C(O)-NH-CH₂-(4-pyridyl) |
| II-15 | 3-pyridyl | -C(O)-N(CH₃)-CH₂-(4-pyridyl) |
| II-17 | 3-pyridyl | -C(O)-NH-CH₂-(4-pyridyl) |
| II-18 | 3-chlorophenyl | -C(O)-NH-(2-hydroxyindan-1-yl) |

-continued
| No. | R¹ | Q—R² |
|---|---|---|
| II-19 | 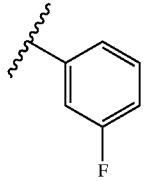 | 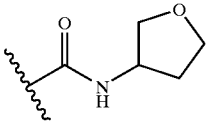 |
| II-21 | 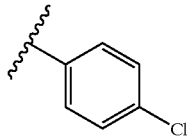 | 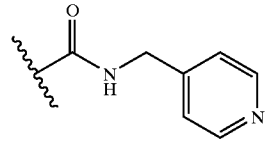 |
| II-22 | 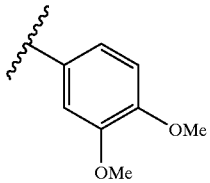 | 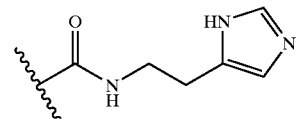 |
| II-23 | 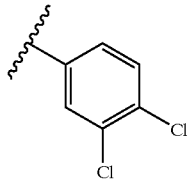 | 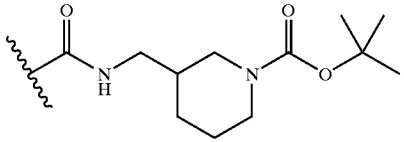 |
| II-24 | 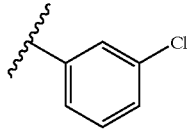 | 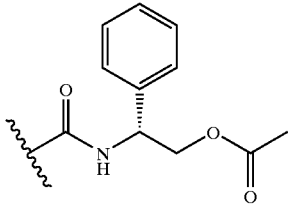 |
| II-25 | 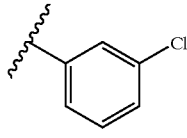 | 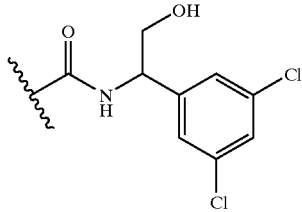 |
| II-26 | 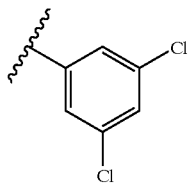 | 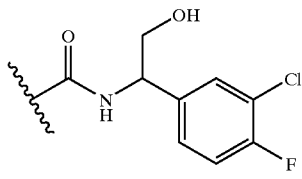 |

-continued

| No. | R¹ | Q—R² |
|---|---|---|
| II-27 | ethylsulfonamido-methyl-(2-chloro)phenyl group | -C(O)NH-CH(Ph)-CH₂OH |
| II-28 | H | -C(O)NH-CH₂-(4-pyridyl) |

13. The compound according to claim 2 wherein said compound is selected from any one of the following compounds:

| No. | T | R¹ | Q—R² |
|---|---|---|---|
| II-29 | NH | 3-pyridyl | -C(O)NH-CH₂-(2-methyl-4-pyridyl) |
| II-30 | NH | 3-pyridyl | -C(O)NH-CH₂-(4-pyridyl) |
| II-31 | NH | 4-piperidinyl | -C(O)NH-CH₂-(3-chloro-4-pyridyl) |
| II-32 | NH | 1H-pyrazol-4-yl | -C(O)NH-CH₂-(4-pyridyl) |
| II-33 | NH | 3-pyridyl | -C(O)N(CH₃)-phenyl |
| II-34 | NH | isopropyl | -C(O)NH-CH₂-(4-pyridyl) |

-continued
| No. | T | R¹ | Q—R² |
|---|---|---|---|
| II-35 | NH | 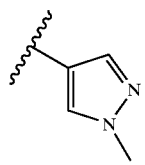 | 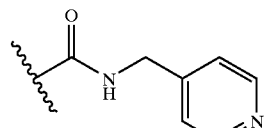 |
| II-36 | NH | 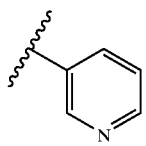 | 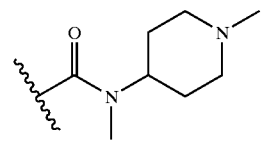 |
| II-37 | NH | CF₃ | 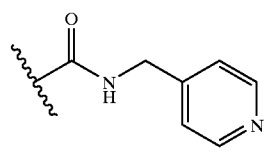 |
| II-38 | NH | 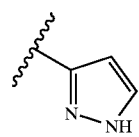 | 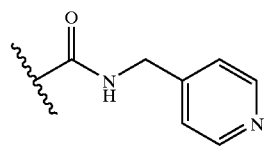 |
| II-39 | NH | 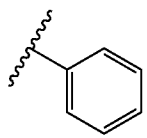 | 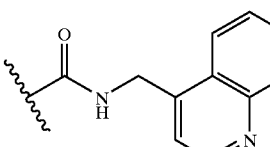 |
| II-40 | NH | 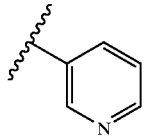 | 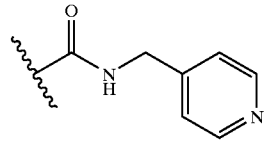 |
| II-42 | NH | 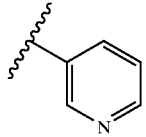 | 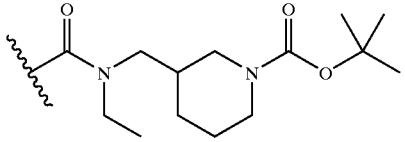 |
| II-43 | NH | 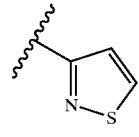 | 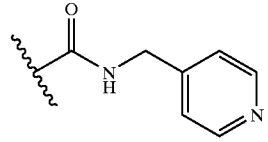 |
| II-44 | NH | 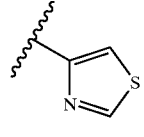 | 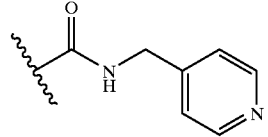 |

-continued

| No. | T | R¹ | Q—R² |
|---|---|---|---|
| II-45 | NHNH | 3-pyridyl | -C(=O)NH-CH₂-(4-pyridyl) |
| II-46 | NHCO | 3-pyridyl | -C(=O)NH-CH₂-(4-pyridyl) |
| II-47 | NHSO₂ | 3-pyridyl | -C(=O)NH-CH₂-(4-pyridyl) |
| II-48 | NH | 3-pyridyl | -C(=O)NH-CH₂-(4-pyridyl) |
| II-49 | NH | 3-pyridyl | -C(=O)N(CH₃)-CH₂-(4-pyridyl) |
| II-50 | NH | 3-pyridyl | -C(=O)N(CH₃)-CH₂-(4-pyridyl) |
| II-51 | NH | 3-pyridyl | -C(=O)N(CH₃)-CH₂-(4-pyridyl) |
| II-52 | NH | 3-pyridyl | -C(=O)N(CH₃)-CH₂-(4-pyridyl) |
| II-53 | NH | 2,6-difluorophenyl | -C(=O)-(piperazin-1-yl) |

-continued
| No. | T | R¹ | Q—R² |
|---|---|---|---|
| II-54 | NH | 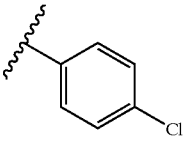 | 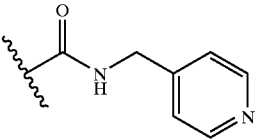 |
| II-55 | NH | 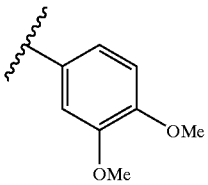 | 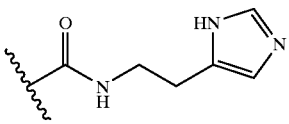 |
| II-56 | NH | 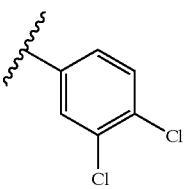 | 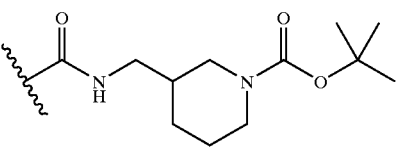 |
| II-57 | NH | 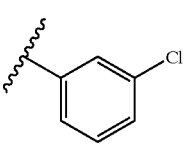 | 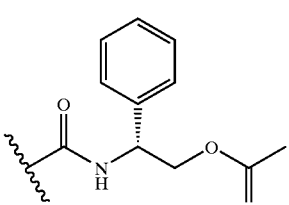 |
| II-58 | NH | 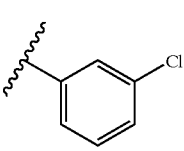 | 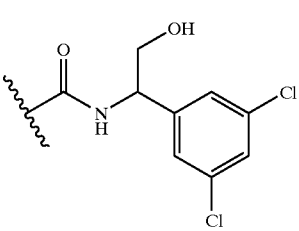 |
| II-59 | NH | 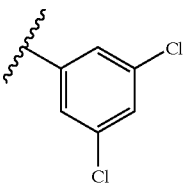 | 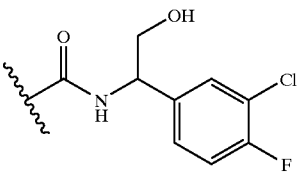 |
| II-60 | NH | 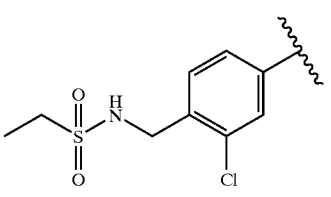 | 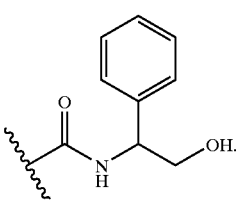 |

14. The compound according to claim 2 wherein said compound is selected from any one of the following compounds:

| No. | T$_n$—R$^1$ | Q—R$^2$ |
|---|---|---|
| II-61 | 2-F-3-Cl-phenyl | *N-methyl-N-[(1R,2S)-2-hydroxy-1-methyl-2-phenylethyl]amide* |
| II-62 | methyl | *N-[(R)-2-hydroxy-1-phenylethyl]amide* |
| II-63 | methyl | *N-[(R)-3-hydroxy-1-phenylpropyl]amide* |
| II-64 | Methyl | *N-[(S)-3-hydroxy-1-phenylpropyl]amide* |
| II-65 | 3,5-dichlorophenyl | *N-[(S)-2-hydroxy-1-phenylethyl]amide* |
| II-66 | 3-F,5-CF$_3$-phenyl | *N-[(S)-2-hydroxy-1-phenylethyl]amide* |
| II-67 | Methyl | *N-[(S)-2-hydroxy-1-phenylethyl]amide* |
| II-68 | H | *N-methyl-N-[(1S,2R)-2-hydroxy-1-methyl-2-phenylethyl]amide* |

-continued
| No. | $T_n$—$R^1$ | Q—$R^2$ |
|---|---|---|
| II-69 | Methyl | 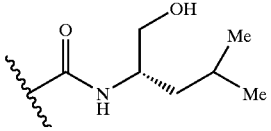 |
| II-70 | Methyl | 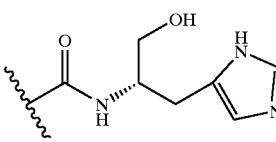 |
| II-71 | Methyl | 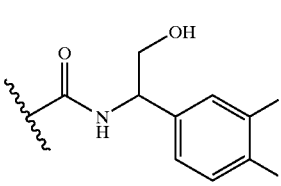 |
| II-72 | Cyclohexyl | 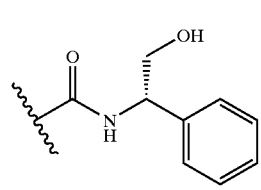 |
| II-73 | Cyclopropyl | 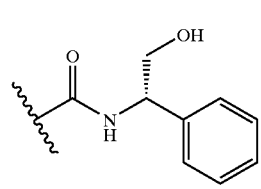 |
| II-74 | Methyl | 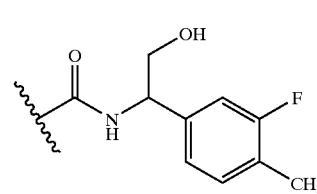 |
| II-75 | Methyl | 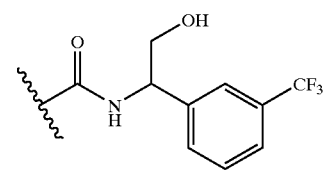 |
| II-76 | $CH_2OCH_3$ | 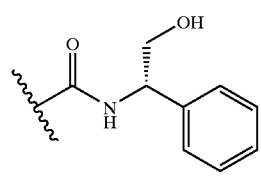 |
| II-77 | $CH_2OH$ | 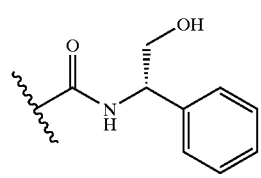 |

-continued

| No. | $T_n$—$R^1$ | Q—$R^2$ |
|---|---|---|
| II-78 | Methyl | amide-NH-CH(CH$_3$)-CH(OH)-phenyl |
| II-79 | Methyl | amide-NH-CH(CH$_3$)-CH(OH)-phenyl (different stereochem) |
| II-80 | Methyl | amide-NH-CH$_2$-CH(OH)-phenyl |
| II-81 | Methyl | amide-NH-CH(CH$_2$OH)-CH(OH)-phenyl |
| II-82 | Methyl | amide-NH-CH(CH$_2$OH)-CH(OH)-phenyl (different stereochem) |
| II-83 | H | amide-NH-CH(CH$_3$)-CH(OH)-phenyl |
| II-84 | H | amide-NH-CH(CH$_3$)-CH(OH)-phenyl (different stereochem) |
| II-85 | H | amide-N(CH$_3$)-CH$_2$-CH(OH)-phenyl |
| II-86 | H | amide-N(CH$_3$)-CH$_2$-CH(OH)-phenyl (different stereochem) |
| II-87 | H | amide-N(CH$_3$)-CH(CH$_3$)-CH(OH)-phenyl |

-continued
| No. | T$_n$—R$^1$ | Q—R$^2$ |
|---|---|---|
| II-88 | H | 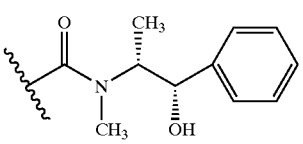 |
| II-89 | Methyl | 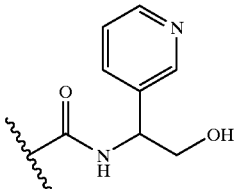 |
| II-90 | Methyl | 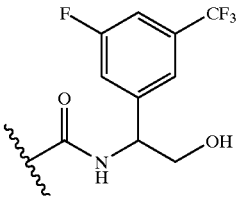 |
| II-91 | Methyl | 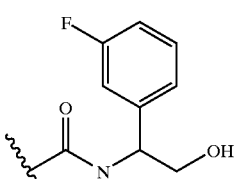 |
| II-92 | Methyl | 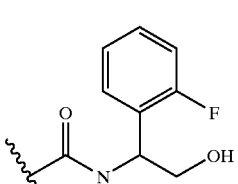 |
| II-93 | Methyl | 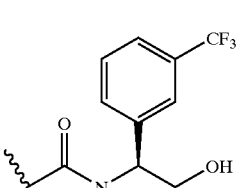 |
| II-94 | Methyl | 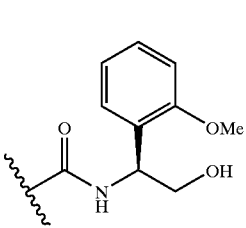 |

-continued

| No. | Tₙ—R¹ | Q—R² |
|---|---|---|
| II-95 | Methyl | (S)-N-(2-hydroxy-1-(3-chlorophenyl)ethyl)amide |
| II-96 | Methyl | (S)-N-(2-hydroxy-1-(3-methylphenyl)ethyl)amide |
| II-97 | Methyl | (S)-N-(2-hydroxy-1-(3-fluorophenyl)ethyl)amide |
| II-98 | Methyl | N-(2-amino-1-(3-chlorophenyl)ethyl)amide |
| II-99 | methyl | N-(3-amino-1-(3-chlorophenyl)propyl)amide |
| II-100 | H | N-(2-amino-1-(3-chlorophenyl)ethyl)amide |
| II-101 | H | N-(3-amino-1-(3-chlorophenyl)propyl)amide |

-continued
| No. | Tₙ—R¹ | Q—R² |
|---|---|---|
| II-102 | 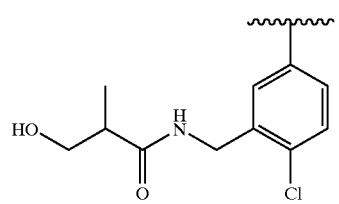 | 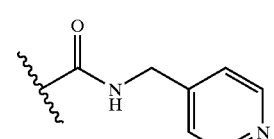 |
| II-103 | 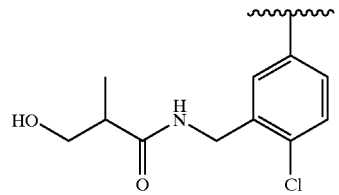 | 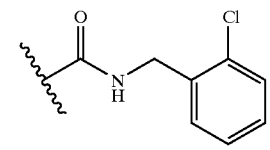 |
| II-104 | 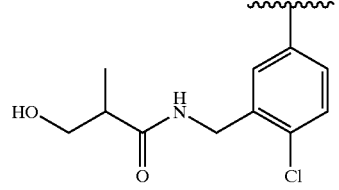 | 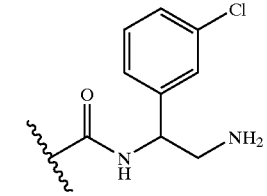 |
| II-105 | 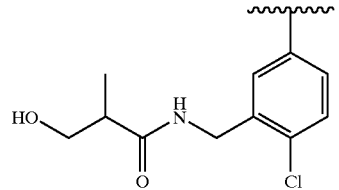 | 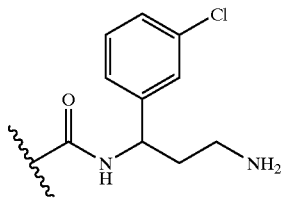 |
| II-106 | 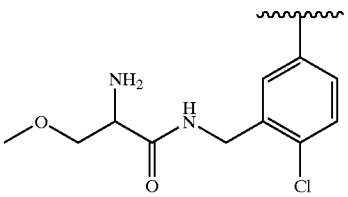 | 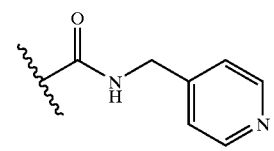 |
| II-107 | 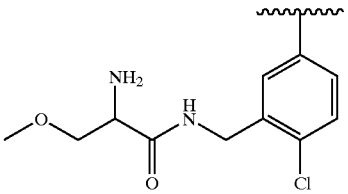 | 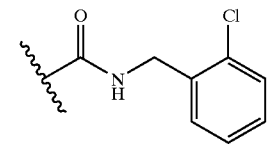 |
| II-108 | 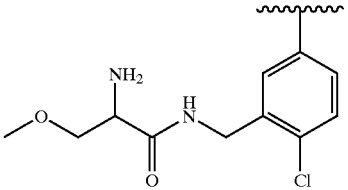 | 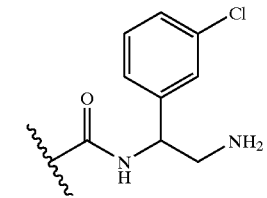 |

| No. | $T_n$—$R^1$ | Q—$R^2$ |
|---|---|---|
| II-109 | 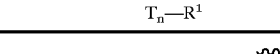 | 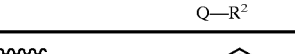 |

15. A composition comprising a compound according to claim 1 in an amount to detectably inhibit ERK kinase activity, and a pharmaceutically acceptable carrier, adjuvant, or vehicle.

16. The composition according to claim 15, additionally comprising an additional therapeutic agent selected from an anti-proliferative agent, an anti-inflammatory agent, an immunomodulatory agent, a neurotrophic factor, an agent for treating cardiovascular disease, an agent for treating liver disease, an anti-viral agent, an agent for treating blood disorders, an agent for treating diabetes, or an agent for treating immunodeficiency disorders.

17. A method of inhibiting ERK kinase activity in a biological sample comprising the step of contacting said biological sample with:
  a) a compound according to claim 1; or
  b) a composition according to claim 15.

18. A method of treating or lessening the severity of an ERK-mediated disease or condition in a is patient comprising the step of administering to said patient a composition according to claim 15.

19. A method of treating or lessening the severity of an cancer, stroke, diabetes, hepatomegaly, cardiovascular disease, Alzheimer's disease, cystic fibrosis, viral disease, autoimmune diseases, atherosclerosis, restenosis, psoriasis, allergic disorders, inflammation, neurological disorders, a hormone-related disease, conditions associated with organ transplantation, immunodeficiency disorders, destructive bone disorders, proliferative disorders, infectious diseases, conditions associated with cell death, thrombin-induced platelet aggregation, chronic myelogenous leukemia (CML), liver disease, pathologic immune conditions involving T cell activation, or CNS disorders, comprising the step of administering to said patient a composition according to claim 15.

20. The method according to claim 19, wherein said method is used to treat cancer.

21. The method according to claim 20, wherein said method is used to treat or prevent a cancer selected from breast; ovary; cervix; prostate; testis, genitourinary tract; esophagus; larynx, glioblastoma; neuroblastoma; stomach; skin, keratoacanthoma; lung, epidermoid carcinoma, large cell carcinoma, small cell carcinoma, lung adenocarcinoma; bone; colon, adenoma; pancreas, adenocarcinoma; thyroid, follicular carcinoma, undifferentiated carcinoma, papillary carcinoma; seminoma; melanoma; sarcoma; bladder carcinoma; liver carcinoma and biliary passages; kidney carcinoma; myeloid disorders; lymphoid disorders, Hodgkin's, hairy cells; buccal cavity and pharynx (oral), lip, tongue, mouth, pharynx; small intestine; colon-rectum, large intestine, rectum; brain and central nervous system; or leukemia.

22. The method according to claim 19, wherein said method is used to treat cardiovascular disease.

23. The method according to claim 22, wherein said method is used to treat a cardiovascular disease selected from restenosis, cardiomegaly, artherosclerosis, myocardial infarction, or congestive heart failure.

24. The method according to claim 19, wherein said method is used to treat neurodegenerative disease selected from Alzheimer's disease, Parkinson's disease, amyotrophic lateral sclerosis, Huntington's disease, cerebral ischemia or neurodegenerative disease caused by traumatic injury, glutamate neurotoxicity or hypoxia.

25. The method according to claim 19, comprising the additional step of administering to said patient an additional therapeutic agent selected from an anti-proliferative agent, an anti-inflammatory agent, an immunomodulatory agent, a neurotrophic factor, an agent for treating cardiovascular disease, an agent for treating liver disease, an anti-viral agent, an agent for treating blood disorders, an agent for treating diabetes, or an agent for treating immunodeficiency disorders, wherein:
  said additional therapeutic agent is appropriate for the disease being treated; and
  said additional therapeutic agent is administered together with said composition as a single dosage form or separately from said composition as part of a multiple dosage form.

26. A composition for coating an implantable device comprising a compound according to claim 1 and a carrier suitable for coating said implantable device.

27. An implantable device coated with a composition according to claim 26.

28. A compound of formula II

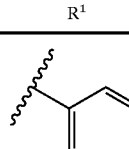

wherein n is 0 and wherein said compound is selected from any of the following compounds:

| No. | n | T | $R^1$ | Q—$R^2$ |
|---|---|---|---|---|
| II-12 | 0 | — | 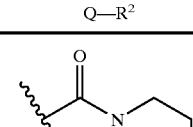 |  |

-continued
| No. | n | T | R¹ | Q—R² |
|---|---|---|---|---|
| II-16 | 0 | — | 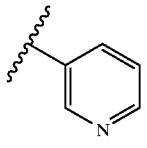 | 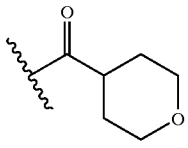 |
| II-20 | 0 | — | 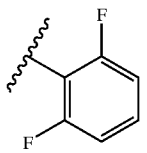 | 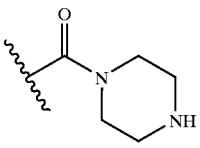 |
-continued
| No. | n | T | R¹ | Q—R² |
|---|---|---|---|---|
| II-41 | 1 | NH | 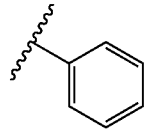 | 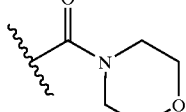 |
* * * * *